United States Patent
Kearney et al.

(10) Patent No.: US 12,233,181 B2
(45) Date of Patent: Feb. 25, 2025

(54) SYSTEMS AND METHODS FOR MONITORING DISINFECTION OF A DEVICE

(71) Applicant: Hand Held Products, Inc., Fort Mill, SC (US)

(72) Inventors: Sean Kearney, Marlton, NJ (US); Marinedrive Piskaladhanabalan, Charlotte, NC (US)

(73) Assignee: Hand Held Products, Inc., Fort Mill, SC (US)

( * ) Notice: Subject to any disclaimer, the term of this patent is extended or adjusted under 35 U.S.C. 154(b) by 1258 days.

(21) Appl. No.: 16/932,254

(22) Filed: Jul. 17, 2020

(65) Prior Publication Data

US 2022/0016293 A1    Jan. 20, 2022

(51) Int. Cl.
*A61L 2/24*      (2006.01)
*A61L 2/28*      (2006.01)

(52) U.S. Cl.
CPC .......... *A61L 2/28* (2013.01); *A61L 2/24* (2013.01); *A61L 2202/14* (2013.01); *Y10S 700/00* (2013.01)

(58) Field of Classification Search
CPC .......... A61L 2/28; A61L 2/24; A61L 2202/14; A61L 2/0082; A61L 2/0088; A61L 2/0094; A61L 2/18; A61L 2/20; A61L 2/22; A61L 2/26; A61L 2202/15; Y10S 700/00
See application file for complete search history.

(56) References Cited

U.S. PATENT DOCUMENTS

| 9,752,999 B2 | 9/2017 | Kalinichev et al. |
| 10,004,823 B2 | 6/2018 | Reid et al. |
| 2006/0180450 A1 | 8/2006 | Clark et al. |

(Continued)

FOREIGN PATENT DOCUMENTS

| AU | 2017234381 A1 | 10/2018 |
| AU | 2018347409 A1 | 5/2020 |

(Continued)

OTHER PUBLICATIONS

Extended European search report Mailed on Dec. 17, 2021 for EP Application No. 21185169, 8 pages.

(Continued)

*Primary Examiner* — Tameem D Siddiquee
(74) *Attorney, Agent, or Firm* — Alston & Bird LLP

(57) ABSTRACT

Various embodiments illustrated herein disclose a method for monitoring disinfection of a device. The method includes receiving sensor data from a plurality of sensors positioned at a respective plurality of surfaces of the device. The sensor data indicates that a disinfecting agent is applied on one or more surfaces of the plurality of surfaces of the device. The method further includes determining at least one exposure characteristic based on the sensor data. The at least one exposure characteristic is associated with disinfection of the one or more surfaces of the device by the disinfecting agent. The method further includes comparing the at least one exposure characteristic to a threshold parameter associated with the at least one exposure characteristic. In response to the comparison, the method further includes generating a notification indicating that the one or more surfaces of the device are disinfected.

15 Claims, 13 Drawing Sheets

(56) References Cited

U.S. PATENT DOCUMENTS

| | | | |
|---|---|---|---|
| 2007/0008147 | A1 | 1/2007 | Bolling |
| 2012/0206384 | A1* | 8/2012 | Marsden .................. G06F 3/023 345/173 |
| 2020/0101183 | A1* | 4/2020 | Dijkstra ..................... A61L 2/28 |
| 2021/0298703 | A1* | 9/2021 | Vestevich ............ A61B 6/4423 |

FOREIGN PATENT DOCUMENTS

| | | |
|---|---|---|
| CN | 101496072 A | 7/2009 |
| CN | 105740130 A | 7/2016 |
| CN | 107823678 A | 3/2018 |
| CN | 111365786 A | 7/2020 |
| WO | 2006/032867 A1 | 3/2006 |
| WO | 2017/093484 A1 | 6/2017 |
| WO | 2019/178639 A1 | 9/2019 |

OTHER PUBLICATIONS

CN Office Action Mailed on Oct. 23, 2023 for CN Application No. 202110681593, 12 page(s).
English Translation of CN Office Action dated Oct. 23, 2023 for CN Application No. 202110681593, 11 page(s).
CN Office Action, including Search Report, Mailed on Dec. 2, 2022 for CN Application No. 202110681593.
English Translation of CN Office Action, including Search Report, Mailed on Dec. 2, 2022 for CN Application No. 202110681593.
Intention to grant Mailed on Oct. 28, 2022 for EP Application No. 21185169.
CN Office Action Mailed on May 31, 2023 for CN Application No. 202110681593, 12 page(s).
English Translation of CN Office Action dated May 31, 2023 for CN Application No. 202110681593, 14 page(s).
Extended European Search Report Mailed on Jun. 20, 2023 for EP Application No. 23159795, 5 page(s).
Decision to grant a European patent Mailed on Mar. 16, 2023 for EP Application No. 21185169.
CN Office Action, including Search Report Mailed on Jun. 28, 2024 for CN Application No. 202110681593, 19 page(s).
CN Reexamination Decision (granted) Mailed on May 7, 2024 for CN Application No. 202110681593, 1 page(s).
English Translation of CN Office Action, including Search Report dated Jun. 28, 2024 for CN Application No. 202110681593, 18 page(s).
English Translation of CN Reexamination Decision (granted) dated May 7, 2024 for CN Application No. 202110681593, 1 page(s).
Swami, Ananthram, et al. (Editors), "Wireless Sensor Networks: Signal Processing and Communications Perspectives," Oct. 2, 2007, John Wiley & Sons, Ltd, retrieved from the Internet at https://uodiyala.edu.iq/uploads/PDF%20ELIBRARY%20UODIYALA/EL37/Wireless%20Sensor%20Networks%20Signal%20Processing%20and%20Communications.pdf on Jul. 24, 2024, 413 pages.
Decision to grant a European patent Mailed on Aug. 8, 2024 for EP Application No. 23159795, 2 page(s).
CN Notice of Acceptance of Reexamination Request Mailed on Feb. 18, 2024 for CN Application No. 202110681593, 1 page(s).
Communication about intention to grant a European patent Mailed on Apr. 3, 2024 for EP Application No. 23159795, 6 page(s).
English Translation of CN Notice of Acceptance of Reexamination Request dated Feb. 18, 2024 for CN Application No. 202110681593, 1 page(s).

* cited by examiner

SYSTEMS AND METHODS FOR MONITORING DISINFECTION OF A DEVICE

TECHNICAL FIELD

Example embodiments of the present disclosure relate generally to a device and, more particularly, to systems and methods for monitoring disinfection of a device.

BACKGROUND

In recent times, the outbreak of contagious diseases has aggravated the risks associated with cross-contamination of commonly touched surfaces of devices such as smartphones, tablets, portable computers, etc., that further spearhead the onset of pandemics.

BRIEF SUMMARY

Exemplary embodiments of the present disclosure relate generally to a device comprising a plurality of sensors and, more particularly, to a method, a device, and a server for monitoring disinfection of the device comprising the plurality of sensors.

Various embodiments illustrated herein disclose a method for monitoring disinfection of a device. The method is performed by a processor of the device. The method comprises receiving sensor data from a plurality of sensors positioned at a respective plurality of surfaces of the device. The sensor data indicates that there is a disinfecting agent applied on one or more surfaces of the plurality of surfaces of the device. The method further comprises determining at least one exposure characteristic based on the sensor data. The at least one exposure characteristic is associated with disinfection of the one or more surfaces of the device by the disinfecting agent. The method further comprises comparing the at least one exposure characteristic to a threshold parameter associated with the at least one exposure characteristic. In response to the comparison, the method further comprises generating a notification indicating that the one or more surfaces of the device are disinfected.

Various embodiments illustrated herein disclose a device comprising a plurality of sensors and a processor communicatively coupled to the plurality of sensors. The plurality of sensors is positioned at a respective plurality of surfaces of the device. The plurality of sensors is configured to generate sensor data that indicates a disinfecting agent is applied on one or more surfaces of the plurality of surfaces of the device. The processor is configured to receive the sensor data from the plurality of sensors. The processor is configured to determine at least one exposure characteristic based on the sensor data. The at least one exposure characteristic is associated with disinfection of the one or more surfaces of the device by the disinfecting agent. The processor is further configured to compare the at least one exposure characteristic to a threshold parameter associated with the at least one exposure characteristic. In response to the comparison, the processor is further configured to generate a notification indicating that the one or more surfaces of the device are disinfected.

Various embodiments illustrated herein disclose a server comprising a processor. The server is communicatively coupled to a device via a network 106. The processor is configured to receive, from the device via the network 106, sensor data from a plurality of sensors positioned at a respective plurality of surfaces of the device. The sensor data indicates that a disinfecting agent is applied on one or more surfaces of the plurality of surfaces of the device. The processor is further configured to determine at least one exposure characteristic based on the sensor data. The at least one exposure characteristic is associated with disinfection of the one or more surfaces of the device by the disinfecting agent. The processor is further configured to compare the at least one exposure characteristic to a threshold parameter associated with the at least one exposure characteristic. In response to the comparison, the processor is further configured to generate a notification indicating that the one or more surfaces of the device are disinfected.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF DRAWINGS

The description of the illustrative embodiments can be read in conjunction with the accompanying figures. It will be appreciated that for simplicity and clarity of illustration, elements illustrated in the figures have not necessarily been drawn to scale. For example, one or more dimensions of some of the elements are exaggerated relative to other elements. Embodiments incorporating teachings of the present disclosure are shown and described with respect to the figures presented herein, in which.

DETAILED DESCRIPTION

Figure 1:
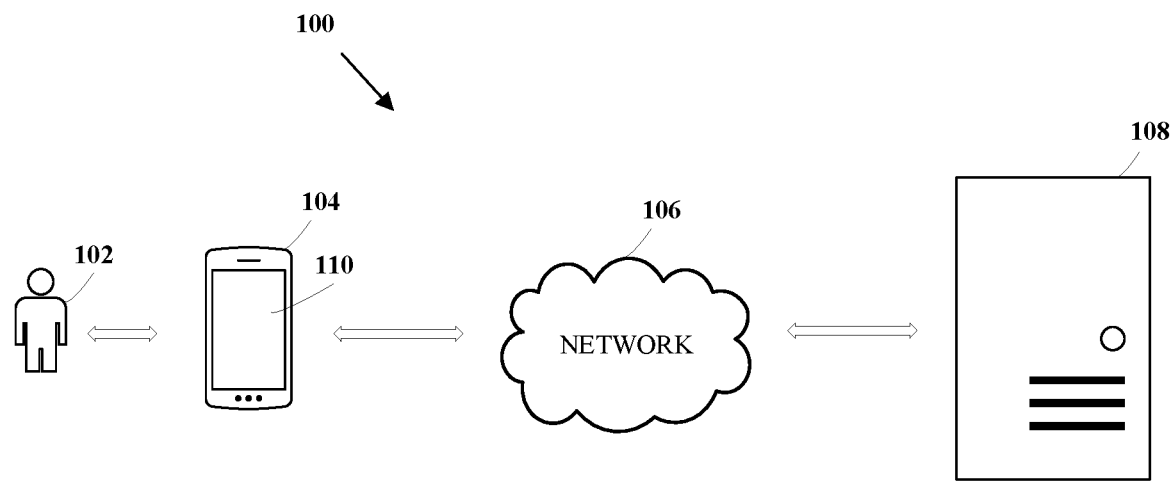
FIG. 1 illustrates an example work environment, according to one or more embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The term "comprising" means including but not limited to, and should be interpreted in the manner it is typically used in the patent context. Use of broader terms such as comprises, includes, and having should be understood to provide support for narrower terms such as consisting of, consisting essentially of, comprised substantially of, etc.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In work environments, such as warehouses, retails stores, material handling environments, hospitals, spas, restaurants, hotels, amusement parks, malls, and/or the like, a user may have move around the facility to perform various operations such as, but not limited to, carrying objects, picking objects from racks, scanning the objects, dimensioning the objects, disease diagnostic activities, customer registration, and/or the like. Typically, the user may utilize devices such as a mobile device, a portable computer, a mobile computer, a handheld computer, a scanning device, a smartphone, a tablet computer, an indicia reader (such as a barcode scanner), or any other portable device, to perform the aforementioned operations. A typical device may include a display screen that may be configured to display tasks for the user to perform. The user may further provide inputs through the display screens to update the status of the tasks being processed by the user. For instance, the user may provide the input through the display screen to mark a task complete. Further, the device may include one or more buttons configured to facilitate the user to provide inputs to the device. For example, the user may press a button to reduce the volume of an audio signal generated by the device, to switch ON or switch OFF the display screen, to switch ON or switch OFF the device, etc. Consequently, the device receives multiple touch inputs from the user on multiple surfaces of the device during a typical use of the device by the user.

Frequent use of such devices in our day-to-day activities results in accumulation of bacteria or viruses on surfaces of the devices, which may result in spread of diseases as and when such devices are exchanged between different users for accomplishing daily routine tasks. Hence, it is imperative to ensure complete sanitization of surfaces of devices to inhibit the propagation of such bacterial or viral diseases via device surfaces.

According to one or more embodiments described herein a device comprising a plurality of sensors is disclosed. The plurality of sensors can be positioned at a respective plurality of surfaces of the device to generate sensor data that indicates that a disinfecting agent is applied on one or more surfaces of the plurality of surfaces of the device. The disinfecting agent may refer to a cleaning solution that is used to kill microorganisms such as bacteria, fungi, viruses, etc., present on a contaminated surface, such as surface of a device. In an embodiment, the disinfecting agent may correspond to a solution comprising, for example, water, alcohol such as ethanol, isopropanol, peroxide, hydrogen peroxide, caprylic acid, citric acid, lactic acid, etc. In an example embodiment, the disinfecting agent corresponds to a solution comprising 70% isopropyl alcohol.

The device comprises a processor communicatively coupled to the plurality of sensors. The processor may determine at least one exposure characteristic associated with disinfection of the one or more surfaces of the device by the disinfecting agent based on the sensor data. The processor may compare the at least one exposure characteristic to a threshold parameter associated with the at least one exposure characteristic. In response to the comparison, the processor may generate a notification indicating that the one or more surfaces of the device are disinfected. The processor may display the notification to a user of the device, via a user interface of the device, to indicate that the device is free from any infection and is safe to use.

The systems and methods disclosed herein help in alleviating risks associated with disease transmission through devices that are commonly and frequently used and shared by different users, in performing day-to-day activities. The systems and methods disclosed herein monitor disinfection of a device in real time to ensure that a disinfecting agent is used to sanitize one or more surfaces of the device thoroughly for a predetermined time duration. The systems and methods disclosed herein trigger a notification when one or more contaminated surfaces of a plurality of surfaces of the device is detected by one or more sensors positioned on the one or more contaminated surfaces of the device, thereby ensuring that a user of the device is not exposed to infectious diseases via the one or more contaminated surfaces.

FIG. 1 illustrates an example work environment 100, according to one or more embodiments described herein. The work environment 100 may refer to environments related to, but not limited to, hospitals, clinics, dispensaries, retail stores, educational institutions, office spaces, transportation sector, commercial establishments providing recreational services, manufacturing of items, inventory storage of the items, packaging and unpackaging of the items, preparing customer orders, recording items related information based on scanning and identification of the items, shipment processing (including shipping and logistics distribution of the items), etc. In the hospital work environment 100, many users 102 perform different operations, which may involve handling of the items during various phases (including, but not limited to, hospitalization, disease diagnosis, various diagnostic tests, etc.), of the overall operational cycle of the hospital work environment 100. For example, the users 102 are involved in registering patient information at the time of hospitalization. In another example, the users 102 may handle performing various diagnostic tests such as, X-rays, CT scans, ultrasound test, etc. In some work environments 100, users 102 may use devices (e.g., a device 104) like personal digital assistants (PDAs), mobile devices, smartphones, or tables that may be used for performing above mentioned operations. Thus, in these work environments 100, many users 102 can be involved in performing various operations involving handling of different types of devices 104 and performing operations including interaction with different machines, such as a scanning and identification device, a computer, a tablet, etc.

In the manufacturing work environment 100, many users 102 perform different operations, which may involve handling of the items during various phases (including, but not limited to, accumulation, sortation, scanning and identification, packaging and shipment preparation, etc.), of the overall operational cycle of the manufacturing work environment 100. For example, the users 102 are involved in manual packaging and unpackaging of the items while preparing customer orders for shipping. In another example, the users 102 may handle placing of the items in an accumulation zone of a conveyor system for automated packaging of the items. In some work environments 100, users 102 may use devices (e.g., a device 104) like personal digital assistants (PDAs) or mobile devices that may be communicatively connected to a headset and a server (e.g., a server 108), for receiving automated or voice directed instructions for performing various operations including scanning and identification of labels, such as barcodes, RFID tags, etc. affixed on the items for shipment preparation. Thus, in these work environments 100, many users 102 are usually involved in performing various operations involving handling of items and performing operations including interaction with different machines, such as an accumulator, a dimensioner, a scanning and identification device, etc., for shipment processing and transportation. As illustrated in FIG. 1, the work environment 100 includes the device 104, a network 106, and a server 108. The device 104 and the server 108 are communicatively coupled with each other through the network 106.

The device 104 corresponds to a computing device that may include suitable logic or circuitry to perform a predetermined operation such as, but is not limited to, executing a predetermined application, scanning a bar code, determining dimensions of an object, displaying an instruction to a user 102 of the device 104 to perform a task, communicating with other devices (e.g., the server 108) through the network 106, executing word processing applications, performing medical diagnostic activities, etc. In an example embodiment, the device 104 may include a display screen 110. The display screen 110 may be configured to display information/content to the user 102 of the device 104. For example, the device 104 may be configured to display instructions on the display screen 110 to the user 102 based on which the user 102 of the device 104 may perform a task. Some examples of the device 104 may include, but are not limited to, a mobile phone, a computer, a laptop, a bar code scanner, palm top computers, PDA, a tablet, a smartphone, and/or any other device that includes the display screen 110. The device 104 is not limited to an electronic device comprising a display screen 110 but may refer to any device, comprising a plurality of sensors 312, 314, 316, and 318 (exemplarily illustrated in FIG. 3), that is used by a user 102 for performing day-to-day activities. In an embodiment, the plurality of sensors 312, 314, 316, and 318 comprise, for example, touch sensors, light sensors, and/or the like. The structure of the device 104 and respective functions of the plurality of sensors 312, 314, 316, and 318 are described later in conjunction with FIG. 3.

The network 106 may be any means such as a device or circuitry embodied in either hardware or a combination of hardware and software that is configured to receive and/or transmit data to/from various devices of the work environment 100 (e.g., the device 104 and the server 108). In this regard, the network 106 may include, for example, a network interface for enabling communications with a wired or wireless communication network. For example, the network 106 may include one or more network interface cards, antennae, buses, switches, routers, modems, and supporting hardware and/or software, or any other device suitable for enabling communications via the network 106. Additionally, or alternatively, the network 106 may include the circuitry for interacting with the antenna(s) to cause transmission of signals via the antenna(s) or to handle receipt of signals received via the antenna(s). Such signals may be transmitted using one or more communication protocols, such as Bluetooth® v1.0 through v3.0, Bluetooth Low Energy (BLE), infrared wireless (e.g., IrDA), ultra-wideband (UWB), induction wireless transmission, Wi-Fi, Near Field Communications (NFC), TCP/IP, UDP, 2G, 3G, 4G, 5G, Worldwide Interoperability for Microwave Access (WiMAX), or other communications protocols.

The server 108 may include suitable logic and/or circuitry that may be configured to receive/transmit data from/to the device 104 through the network 106. For example, the server 108 may be configured to generate a disinfection monitoring dataset based on sensor data received from a plurality of devices 104, train a plurality of disinfection models, derive inferences from the disinfection monitoring dataset for monitoring disinfection of the plurality of devices 104, transmit instructions related to a task to be performed by the user 102 of the device 104, etc. In an example embodiment, the server 108 may be implemented using various known application servers such as, but are not limited to, JBOSS™, Apache™, Apache-Tomcat™, and/or the like. In an embodiment, the server 108 is configured to monitor disinfection of the device 104, as explained in conjunction with FIG. 11.

Figure 2:
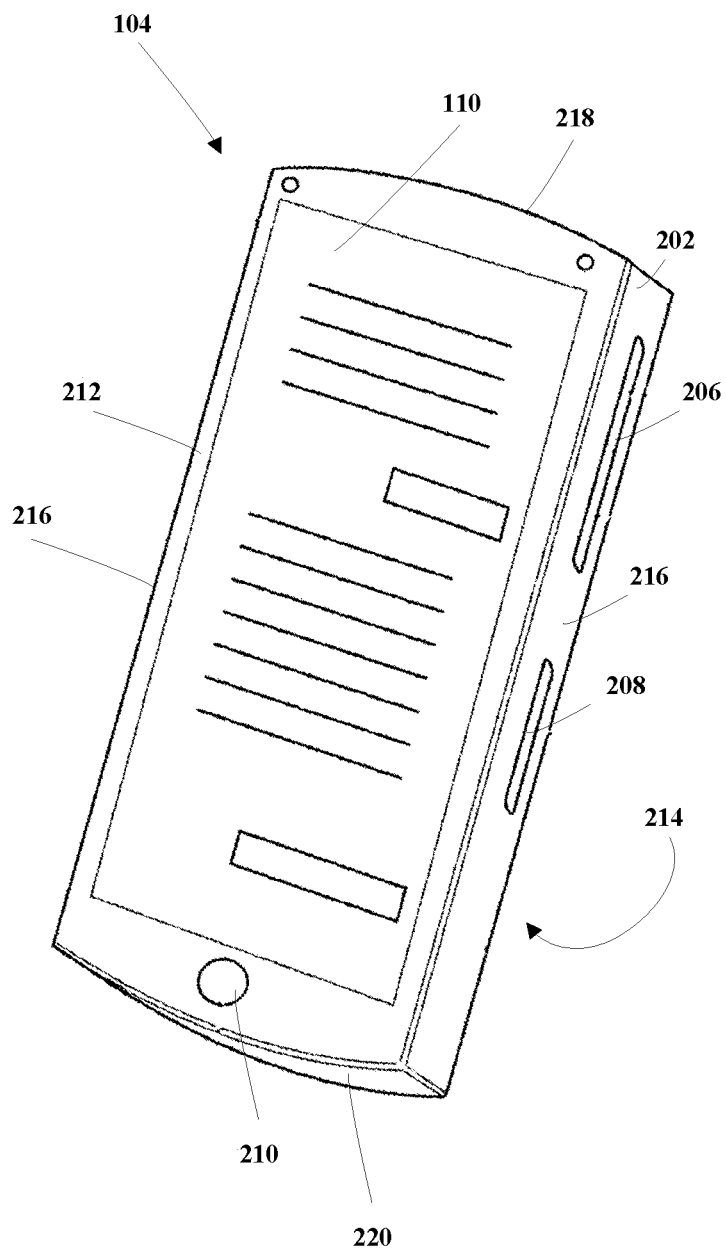
FIG. 2 illustrates a perspective view of a device, according to one or more embodiments described herein.

FIG. 2 illustrates a perspective view of the device 104, according to one or more embodiments described herein. In an example embodiment, the device 104 includes a housing 202, a plurality of sensors 312, 314, 316, and 318 (exemplarily illustrated in FIG. 3), a display screen 110, and one or more buttons 206, 208, and 210. The housing 202 may be configured to receive one or more electronic circuits (not shown) such as, but not limited to, a processor 302 (exemplarily illustrated in FIG. 3), a memory unit 304 (exemplarily illustrated in FIG. 3), a user interface 308 (exemplarily illustrated in FIG. 3), an antenna, a battery, and/or the like that may enable the device 104 to monitor disinfection of the device 104. Further, the housing 202 may be configured to receive the plurality of sensors 312, 314, 316, and 318, the display screen 110, and the one or more buttons 206, 208, and 210. The plurality of sensors 312, 314, 316, and 318 are described later in conjunction with FIG. 3.

The plurality of sensors 312, 314, 316, and 318 comprise, for example, touch sensors, light sensors, and/or the like. The plurality of sensors 312, 314, 316, and 318 can be positioned at a respective plurality of surfaces 212, 214, 216, 218, and 220 of the device 104. The plurality of sensors 312, 314, 316, 318 may include suitable logic, circuitry, interfaces, and/or code that may facilitate monitoring disinfection of the device 104 based on the sensor data generated by the plurality of sensors 312, 314, 316, 318. In an embodiment, the plurality of surfaces 212, 214, 216, 218, and 220 comprises a front surface 212 comprising the display screen 110, a back surface 214, a side surface 216, a top surface 218, a bottom surface 220, etc., as exemplarily illustrated in FIG. 2.

In an embodiment where the plurality of sensors 312, 314, 316, and 318 corresponds to the touch sensors, the plurality of sensors 312, 314, 316, and 318 are configured to detect one or more touch inputs of the user 102 received on one or more surfaces 212, 214, 216, 218, or 220 of the device 104. In an embodiment, the one or more touch inputs may correspond to a user's finger touch, a user's hand or palm touch, one or more taps on a surface 212, 214, 216, 218, or 220 of the device 104, a swiping gesture on a surface such as the front surface 212 of the device 104, a touch input attributed by a cleaning material soaked in the disinfecting agent, etc. The touch sensors comprise, for example, resistive sensors, capacitive touch sensors, ultrasonic or other acoustic sensors, infrared or other optical sensors, piezoelectric touch sensors, etc. In an example embodiment, the touch sensors may correspond to an array of capacitive touch sensors that may be configured to detect the one or more touch inputs based on a change in the capacitance of the array of capacitive touch sensors. In another example embodiment, the touch sensors may correspond to resistive sensors that may be configured to detect the one or more touch inputs based on a change in the resistivity of the resistive sensors. In an embodiment, the sensor data generated by the one or more touchسensors corresponds to data associated with a change in capacitance of the array of capacitive touch sensors, a change in resistivity of the resistive sensors, a location on the display screen 110 or any other surface 212, 214, 216, 218, or 220 of the device 104 where a touch input is detected, etc. In an embodiment, the processor 302 of the device 104 is configured to identify the one or more surfaces 212, 214, 216, 218, and 220 of the device 104 for disinfection by the disinfecting agent based on the sensor data generated by the one or more touch sensors positioned at the locations of the one or more touch inputs, as described further in conjunction with FIG. 6. Further, the processor 302 may be configured to determine whether the one or more surfaces 212, 214, 216, 218, and 220 have been disinfected by the user 102 of the device 104.

In an embodiment where the one or more sensors 312, 314, 316, and 318 corresponds to the light sensor, the light sensor may be utilized to determine whether the plurality of surfaces 212, 214, 216, 218, and 220 of the device 104 has been disinfected. For example, the light sensor may include a light transmitter and a light receiver. When there is no liquid on a surface 212, 214, 216, 218, or 220, the light transmitter may transmit light and the light receiver may not receive any portion of the transmitted light. For instance, the light transmitter may transmit the light to the ambient environment. When the surface 212, 214, 216, 218, or 220 has the liquid, a portion of the light may be reflected towards the light receiver, which is detected by the light receiver. The light receiver may generate the sensor data based on the detected portion of the transmitted light. In another embodiment, the light sensor may not have a light transmitter. In such an embodiment, the light receiver may be configured to generate the sensor data based on the reception of the ambient light. To this end, when the liquid is present on the surface 212, 214, 216, 218, or 220, the ambient light received by the light receiver may get disrupted (because of refraction and/or reflection caused by the liquid on the surface 212, 214, 216, 218, or 220). Accordingly, the sensor data generated by the light receiver may depict the disruption in the received ambient light. For example, amplitude and frequency of the received ambient light captured in the sensor data may vary based on the disruptions in the received ambient light.

In some examples, the device 104 may include both the touch sensors and the light sensors for detecting the moisture on the plurality of surfaces 212, 214, 216, 218, or 220 of the device 104. For example, the touch sensor may be configured to determine which surface 212, 214, 216, 218, or 220 of the plurality of surfaces 212, 214, 216, 218, and 220 requires the disinfection, while the light sensor may be configured to monitor the disinfection of the surface 212, 214, 216, 218, or 220. In another embodiment, both the touch sensor and the light sensor may be used to monitor the disinfection. In yet another embodiment, both the touch sensor and the light sensor may be configured to detect cheat scenarios where a user 102 may try to cheat the process of determining disinfection by touching few areas of the surface 212, 214, 216, 218, or 220 with wet fingers.

The display screen 110 may include suitable logic, circuitry, interfaces, and/or code that may facilitate rendering or displaying content on the display screen 110. In an example embodiment, the display screen 110 may be realized through several known technologies such as, cathode ray tube (CRT) based display, liquid crystal display (LCD), light emitting diode (LED) based display, organic LED display technology, retina display technology, etc. In some embodiments, the display screen 110 may further include a touch panel such as a thermal touch panel, a capacitive touch panel, and/or a resistive touch panel, which may enable the user 102 to provide inputs to the device 104 via the display screen 110.

In an example embodiment, the one or more buttons 206, 208, and 210 are configured to facilitate the user 102 to provide inputs to the device 104. For example, the user 102 may press a button 206 to reduce volume of an audio signal generated by the device 104. In another example, the user 102 may press a button 208 to switch ON or switch OFF the display screen 110. In yet another example, the user 102 may press a button 210 to switch ON or switch OFF the device 104.

Figure 3:
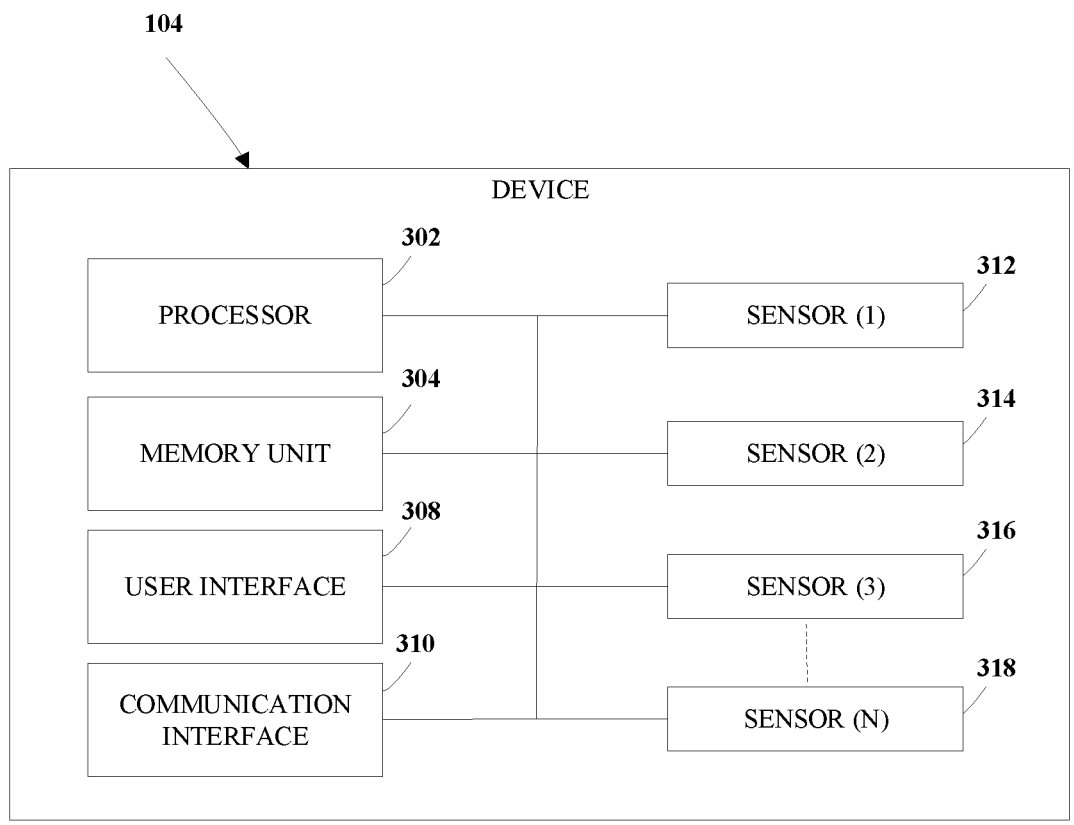
FIG. 3 illustrates a block diagram of the device, according to one or more embodiments described herein.

FIG. 3 illustrates a block diagram of the device 104, according to one or more embodiments described herein. The device 104 comprises a processor 302, a memory unit 304, a user interface 308, a communication interface 310, and a plurality of sensors 312, 314, 316, and 318, as exemplarily illustrated in FIG. 3.

The processor 302 may be embodied as means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 3 as a single processor 302, in an embodiment, the processor 302 may include a plurality of processors and signal processing modules. The plurality of processors may be embodied on a single device 104 or may be distributed across a plurality of devices collectively configured to function as the circuitry of the device 104. The plurality of processors may be in operative communication with each other and may be collectively configured to perform one or more functionalities of the circuitry of the device 104, as described herein. In an example embodiment, the processor 302 may be configured to execute instructions stored in the memory unit 304 or otherwise accessible to the processor 302. These instructions, when executed by the processor 302, may cause the circuitry of the device 104 to perform one or more of the functionalities, as described herein.

Whether configured by hardware, firmware/software methods, or by a combination thereof, the processor 302 may include an entity capable of performing operations according to embodiments of the present disclosure while configured accordingly. Thus, for example, when the processor 302 is embodied as an ASIC, FPGA or the like, the processor 302 may include specifically configured hardware for conducting one or more operations described herein. Alternatively, as another example, when the processor 302 is embodied as an executor of instructions, such as may be stored in the memory unit 304, the instructions may specifically configure the processor 302 to perform one or more algorithms and operations described herein.

Thus, the processor 302 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor 302 dedicated to running other applications. Software applications may be stored in the memory unit 304 before they are accessed and loaded into the processors. The processors may include internal memory sufficient to store the application software instructions. In many devices, the memory unit 304 may be a volatile or nonvolatile memory, such as flash memory, or a mixture of both. The memory unit 304 can also be located internal to another computing resource (e.g., enabling computer readable instructions to be downloaded over the Internet or another wired or wireless connection).

In an example embodiment, the processor 302 may be configured to be communicatively coupled to the plurality of sensors 312, 314, 316, and 318. The plurality of sensors 312, 314, 316, and 318 can be positioned at a respective plurality of surfaces 212, 214, 216, 218, and 220 of the device 104. The plurality of sensors 312, 314, 316, and 318 are configured to generate sensor data. In an embodiment, prior to receiving the sensor data from the plurality of sensors 312, 314, 316, and 318, the processor 302 may be configured to detect one or more touch inputs on one or more surfaces 212, 214, 216, 218, and 220 of a plurality of surfaces 212, 214, 216, 218, and 220 of the device 104. As used herein, the phrase "touch inputs" refers to haptic inputs detected on a surface 212, 214, 216, 218, or 220 of the device 104. In an embodiment, the one or more touch inputs may correspond to a user's finger touch, a user's hand or palm touch, one or more taps on a surface 212, 214, 216, 218, or 220 of the device 104, a swiping gesture on a surface 212 of the device 104, a touch input attributed by a cleaning material soaked in a disinfecting agent, deposition of the disinfecting agent on a surface 212, 214, 216, 218, or 220 of the device 104 by spraying the disinfecting agent, etc. In an embodiment, in response to the detection, the processor 302 may be further configured to activate one or more sensors (e.g., the sensor 312 and 314) positioned at a surface that received the touch input. In another embodiment, the plurality of sensors 312, 314, 316, and 318 positioned at the respective one or more surfaces 212, 214, 216, 218, and 220 of the device 104 may remain in an active state to generate the sensor data as long as the device 104 remains powered on.

In an embodiment, the sensor data indicates that a disinfecting agent is applied on the plurality of surfaces 212, 214, 216, 218, and 220 of the device 104. In some examples, the sensor data may correspond to a voltage signal with varying amplitude. The varying amplitude of the sensor data may indicate moisture accumulation on the plurality of surfaces 212, 214, 216, 218, or 220. In some examples, the scope of the disclosure is not limited to the sensor data corresponding to the voltage signal. In an example embodiment, the sensor data may correspond to a capacitance signal indicating a variation in the capacitance of the multiple capacitors in the display screen 110. The variation in the capacitance may indicate the moisture accumulation on the plurality of surfaces 212, 214, 216, 218, or 220.

For the purpose of ongoing description, the sensor data is considered to indicate the voltage signal. However, those having ordinary skills in the art would understand that the embodiments applicable using the voltage signal are also applicable using the sensor data that corresponds to the capacitance signal.

As the moisture evaporates from the surface, the amplitude of the voltage signal changes accordingly. Evaporation rates of different disinfecting agents are different. For example, the evaporation rate of alcohol is faster than the evaporation rate of water. The processor 302 is configured to calculate a rate of change in the amplitude of the voltage signal (i.e., the sensor data) on the surface 212, 214, 216, 218, or 220 to determine the evaporation rate, which indicates a particular disinfecting agent, such as alcohol or water. In an embodiment, where the sensor data corresponds to the capacitance signal, the processor 302 is configured to calculate a rate of change in the capacitance signal (i.e., the sensor data) of the multiple capacitors in the display screen 110 to determine the evaporation rate.

In an embodiment, the device 104 includes means such as, the processor 302 and/or the like, for ensuring error-free determination of the one or more surfaces 212, 214, 216, 218, and 220 that are disinfected by the disinfecting agent. When a surface 212, 214, 216, 218, or 220 is wiped using a disinfecting agent, the moisture content on the surface 212, 214, 216, 218, or 220 affects the capacitance of an entirety of the surface 212, 214, 216, 218, or 220 uniformly. In an example embodiment, if a user 102 is trying to cheat the process of determining disinfection by touching few areas of the surface 212, 214, 216, 218, or 220 with wet fingers, only the sensors 312, 314, 316, and 318 (for example, touch sensors) corresponding to the areas of the surface 212, 214, 216, 218, or 220 that are touched by the wet fingers may detect the moisture content while the rest of the sensors 312, 314, 316, and 318 corresponding to areas of the rest of the surface 212, 214, 216, 218, or 220 that remains dry may not detect the moisture content. Accordingly, since electrical signals generated by each sensor 312, 314, 316, and 318 differs based on each surface 212, 214, 216, 218, or 220 of the plurality of surfaces being wet or dry, the processor 302 uses the sensor data from each of the sensors 312, 314, 316, and 318 to differentiate between areas of the surface 212, 214, 216, 218, or 220 that are wiped with the disinfecting agent and areas of the surface 212, 214, 216, 218, or 220 that are touched with the wet fingers. Accordingly, the processor 302 ensures error-free determination of disinfected and/or contaminated surfaces 212, 214, 216, 218, or 220 of the device 104, as further described in conjunction with FIG. 7.

In another embodiment, prior to receiving the sensor data, the processor 302 may be configured to detect one or more touch inputs on one or more surfaces 212, 214, 216, 218, and 220 of a plurality of surfaces 212, 214, 216, 218, and 220 of the device 104. For example, a sensor (e.g., 318) of the plurality of sensors 312, 314, 316, and 318 corresponding to a capacitive touch sensor detects one or more touch inputs on the display screen 110 of the device 104 based on a change in capacitance of the surface 212 detected by the capacitive touch sensor. When a user 102 touches the display screen 110 at a particular location on the display screen 110, the capacitive touch sensor at the particular location detects a change in the capacitance. Accordingly, the processor 302 detects a touch input at the particular location and determines that the display screen 110 may be contaminated. In response to the detection, the processor 302 may be configured to identify the surface 212 such as the display screen 110 comprising the particular location as the surface 212 for disinfection by the disinfecting agent. The processor 302 may be further configured to generate a notification to indicate the one or more surfaces 212, 214, 216, 218, and 220 for the disinfection by the disinfecting agent. For example, the processor 302 generates a notification to indicate that the front surface 212 comprising the display screen 110 may be contaminated and displays the notification to the user 102 via the user interface 308 of the device 104.

In an embodiment, the processor 302 may be configured to receive the sensor data from the plurality of sensors 312, 314, 316, and 318. The processor 302 may be configured to determine at least one exposure characteristic based on the sensor data, as further described in conjunction with FIGS. 7-9. The at least one exposure characteristic is associated with disinfection of the one or more surfaces 212, 214, 216, 218, and 220 of the device 104 by the disinfecting agent. The processor 302 may be configured to compare the at least one exposure characteristic to a threshold parameter associated with the at least one exposure characteristic. As used herein, the phrase "threshold parameter" may refer to a value of the exposure characteristic below which a surface 212, 214, 216, 218, or 220 of the device 104 is deemed to be contaminated, as further described in conjunction with FIGS. 7-9. In an example embodiment, the threshold parameter is determined by the server 108, as described further in conjunction with FIG. 13. In response to the comparison, the processor 302 may be configured to generate a first notification indicating that the one or more surfaces 212, 214, 216, 218, and 220 of the device 104 are disinfected. Further, in response to the comparison, the processor 302 may be configured to determine at least one contaminated surface of the one or more surfaces 212, 214, 216, 218, and 220 when the at least one exposure characteristic is below the threshold parameter. The processor 302 may be configured to generate a second notification to indicate the at least one contaminated surface 212, 214, 216, 218, or 220 for the disinfection by the disinfecting agent. This embodiment is further described in conjunction with FIG. 4.

In an embodiment, the at least one exposure characteristic comprises a measure of moisture content on the one or more surfaces 212, 214, 216, 218, and 220 of the device 104, a first time duration associated with application of the disinfecting agent on the one or more surfaces 212, 214, 216, 218, and 220 of the device 104, a second time duration between subsequent instances of application of the disinfecting agent on the one or more surfaces 212, 214, 216, 218, and 220 of the device 104, and/or a chemical property of the disinfecting agent. In an embodiment, the processor 302 may be further configured to monitor disinfection of the device 104 based on the comparison of the measure of moisture content to a moisture threshold parameter, as further described in conjunction with FIG. 7. In an embodiment, the processor 302 may be further configured to monitor disinfection of the device 104 based on comparison of the first time duration associated with application of the disinfecting agent on the one or more surfaces 212, 214, 216, 218, and 220 of the device 104 to a time threshold parameter, as further described in conjunction with FIG. 7. In an embodiment, the processor 302 may be further configured to monitor disinfection of the device 104 based on comparison of the second time duration between subsequent instances of application of the disinfecting agent on the one or more surfaces 212, 214, 216, 218, and 220 of the device 104 to a time interval threshold parameter, as further described in conjunction with FIG. 8. In an embodiment, the processor 302 may be further configured to determine a type of the disinfecting agent based on comparison of the chemical property to a reference chemical property stored in a database, as further described in conjunction with FIG. 9. For example, various types of disinfecting agents correspond to, but are not limited to, alcoholic disinfectants such as ethanol, isopropanol, etc., oxidizing disinfectants such as peroxide, hydrogen peroxide, etc., organic acids such as caprylic acid, citric acid, lactic acid, etc. In an embodiment, the disinfecting agent may also refer to water.

In an embodiment, the processor 302 may be further configured to transmit the sensor data to the server 108 via the network 106. In this embodiment, the processor 302 is configured to receive the first notification indicating that the one or more surfaces 212, 214, 216, 218, and 220 of the device 104 are disinfected, from the server 108. In this embodiment, the server 108 is configured to determine the at least one exposure characteristic and to generate the first notification based on the comparison of the at least one exposure characteristic to the threshold parameter. This embodiment is further described in conjunction with FIG. 11.

The memory unit 304 may include suitable logic, circuitry, and/or interfaces that are adapted to store a set of instructions that is executable by the processor 302 to perform predetermined operations. Software applications may be stored in the memory unit 304 before they are accessed and loaded into the processor 302. The processor 302 may include internal memory sufficient to store the application software instructions. In many devices, the memory unit 304 may be a volatile or nonvolatile memory, such as flash memory, or a mixture of both. The memory unit 304 can also be located internal to another computing resource (e.g., enabling computer readable instructions to be downloaded over the Internet or another wired or wireless connection). Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an embodiment, the memory unit 304 may be integrated with the processor 302 on a single chip, without departing from the scope of the disclosure. In an example embodiment, the memory unit 304 may be configured to store data pertaining to the plurality of sensors 312, 314, 316, and 318. In an example embodiment, the data pertaining to the plurality of sensors 312, 314, 316, and 318 may include, but not limited to, a location of each sensor 312, 314, 316, and 318. In an example embodiment, the data pertaining to the plurality of sensors 312, 314, 316, and 318 may include, but not limited to, a location of each sensor 312, 314, 316, and 318. Further, the data includes unique address associated with each sensor 312, 314, 316, and 318. In an example embodiment, the unique address may enable the processor 302 to individually control the plurality of sensors 312, 314, 316, and 318. For example, based on the unique address, the processor 302 may be able to uniquely identify which of the plurality of sensors 312, 314, 316, and 318 has sent an electrical signal (corresponding to the sensor data) to the processor 302.

The user interface 308 may include suitable logic or circuitry that may enable the user interface 308 to communicate with the display screen 110. For example, the user interface 308 may be configured to receive the haptic signal from each sensor 312, 314, 316, and 318 corresponding to a touch sensor in the display screen 110. Further, the user interface 308 may be configured to determine the location of the touch input on the display screen 110. The user interface 308 may be implemented using one or more technologies, such as, but not limited to, FPGA, ASIC, and the like.

The communication interface 310 may facilitate transmission and reception of messages and data to and from various components of the device 104. For example, the communication interface 310 is communicatively coupled with the processor 302, the plurality of sensors 312, 314, 316, and 318, the memory unit 304, and the user interface 308. Examples of the communication interface 310 may include, but are not limited to, an antenna, an Ethernet port, a USB port, a serial port, or any other port that can be adapted to receive and transmit data. The communication interface 310 transmits and receives data and/or messages in accordance with the various communication protocols, such as, I2C, TCP/IP, UDP, 2G, 3G, 4G or 5G communication protocols, etc.

FIGS. 4-9 illustrate example flowcharts 400, 500, 600, 700, 800, and 900 of the operations performed by the device 104 of FIG. 3, in accordance with example embodiments of the present invention. It will be understood that each block of the flowcharts 400, 500, 600, 700, 800, and 900, and combinations of blocks in the flowcharts 400, 500, 600, 700, 800, and 900, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by the memory unit 304 of the device 104 employing an embodiment of the present invention and executed by the processor 302 in the device 104. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 4-9, when executed, convert a computer or processing circuitry into a particular machine configured to perform an example embodiment of the present invention. Accordingly, the operations of FIGS. 4-9 define an algorithm for configuring a computer or a processor, to perform an example embodiment. In some cases, a general-purpose computer may be provided with an instance of the processor 302 which performs the algorithm of FIGS. 4-9 to transform the general-purpose computer into a particular machine configured to perform an example embodiment.

Accordingly, blocks of the flowchart support combinations of means for performing the specified functions and combinations of operations for performing the specified functions. It will also be understood that one or more blocks of the flowcharts' 400, 500, 600, 700, 800, and 900, and combinations of blocks in the flowcharts 400, 500, 600, 700, 800, and 900, can be implemented by special purpose hardware-based computer systems which perform the specified functions, or combinations of special purpose hardware and computer instructions.

Figure 4:
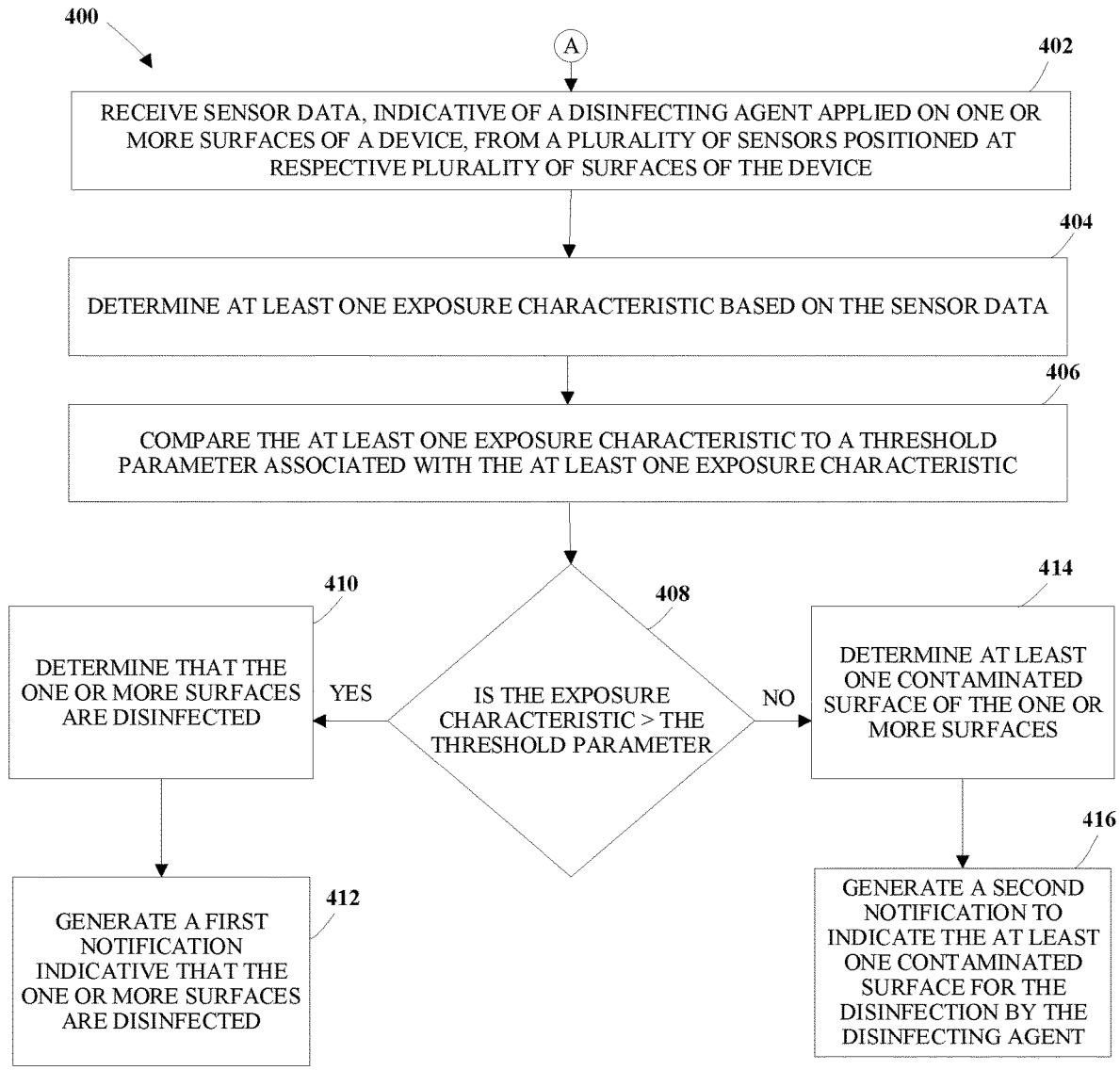
FIG. 4 illustrates a flowchart of a method for monitoring disinfection of the device, according to one or more embodiments described herein.

FIG. 4 illustrates a flowchart 400 of a method for monitoring disinfection of the device 104, according to one or more embodiments described herein. At step 402, the device 104 includes means such as, the processor 302 and/or the like, for receiving sensor data from a plurality of sensors 312, 314, 316, and 318. As discussed in conjunction with FIG. 3, the plurality of sensors 312, 314, 316, and 318 may correspond to touch sensors, light sensors, and/or the like. The plurality of sensors 312, 314, 316, and 318 can be positioned at a respective plurality of surfaces 212, 214, 216, 218, and 220 of the device 104. The sensor data indicates that a disinfecting agent is applied on one or more surfaces 212, 214, 216, 218, and 220 of the plurality of surfaces 212, 214, 216, 218, and 220 of the device 104, as described in conjunction with FIG. 3. In an example embodiment, the disinfecting agent may correspond to a solution comprising, for example, alcohol such as ethanol, isopropanol, water, peroxide, hydrogen peroxide, caprylic acid, citric acid, lactic acid, etc. In an example embodiment, the disinfecting agent corresponds to a solution comprising 70% isopropyl alcohol. As discussed, the sensor data may correspond to the voltage signal, where an amplitude of the voltage signal may vary in accordance with the moisture content on a surface 212, 214, 216, 218, or 220 of the device 104.

At step 404, the device 104 includes means such as, the processor 302 and/or the like, for determining at least one exposure characteristic based on the sensor data. The at least one exposure characteristic is associated with disinfection of the one or more surfaces 212, 214, 216, 218, and 220 of the device 104 by the disinfecting agent. In an embodiment, the at least one exposure characteristic comprises at least one of a measure of moisture content on the one or more surfaces 212, 214, 216, 218, and 220 of the device 104, a first time duration associated with application of the disinfecting agent on the one or more surfaces 212, 214, 216, 218, and 220 of the device 104, a second time duration between subsequent instances of application of the disinfecting agent on the one or more surfaces 212, 214, 216, 218, and 220 of the device 104, a chemical property of the disinfecting agent, etc. The determination of the measure of the moisture content and the first time duration associated with the application of the disinfecting agent is further described in conjunction with FIG. 7. The determination of the second time duration between subsequent instances of application of the disinfecting agent is further described in conjunction with FIG. 8. The determination of the chemical property of the disinfecting agent is further described in conjunction with FIG. 9.

At step 406, the device 104 includes means such as, the processor 302 and/or the like, for comparing the at least one exposure characteristic to a threshold parameter associated with the at least one exposure characteristic. As used herein, the phrase "threshold parameter" may refer to a value of the exposure characteristic below which a surface 212, 214, 216, 218, or 220 of the device 104 is deemed to be contaminated, as described further in conjunction with FIGS. 7-9. In an example embodiment, the threshold parameter is determined by the server 108, as described further in conjunction with FIG. 13. At step 408, the device 104 includes means such as, the processor 302 and/or the like, for determining whether the at least one exposure characteristic exceeds the threshold parameter. For example, the comparison of the measure of the moisture content and the first time duration with respective threshold parameters such as, a moisture threshold parameter and a time threshold parameter, respectively, is further described in conjunction with FIG. 7. In another example, the comparison of the second time duration with a time interval threshold parameter is further described in conjunction with FIG. 8. In another example, the comparison of the chemical property of the disinfecting agent with a threshold parameter such as a reference chemical property is further described in conjunction with FIG. 9.

At step 410, the device 104 includes means such as, the processor 302 and/or the like, for determining that the one or more surfaces 212, 214, 216, 218, and 220 are disinfected when the at least one exposure characteristic exceeds the threshold parameter. For example, when a measure of moisture content exceeds a moisture threshold parameter, the processor 302 determines that the one or more surfaces 212, 214, 216, 218, and 220 are disinfected, as described further in conjunction with FIG. 7. In another example, when a duration of application of a disinfecting agent exceeds a time threshold parameter, the processor 302 determines that the one or more surfaces 212, 214, 216, 218, and 220 are disinfected, as described further in conjunction with FIG. 7. In another example, when a time duration between subsequent instances of application of a disinfecting agent on the one or more surfaces 212, 214, 216, 218, and 220 exceeds a time interval threshold parameter, the processor 302 determines that the one or more surfaces 212, 214, 216, 218, and 220 require disinfection, as described further in conjunction with FIG. 8.

At step 412, the device 104 includes means such as, the processor 302 and/or the like, for generating a first notification indicating that the one or more surfaces 212, 214, 216, 218, and 220 of the device 104 are disinfected, in response to the comparison. In an embodiment, the first notification comprises, for example, a text message, an audio message, a vibration, a color-coded LED indicator, etc. The generation of the first notification based on the comparison of the measure of the moisture content and the first time duration with a moisture threshold parameter and a time threshold parameter, respectively, is further described in conjunction with FIG. 7. The generation of the first notification based on the comparison of the second time duration with a time interval threshold parameter is further described in conjunction with FIG. 8. The generation of the first notification based on the comparison of the chemical property of the disinfecting agent with a reference chemical property is further described in conjunction with FIG. 9.

At step 414, the device 104 includes means such as, the processor 302 and/or the like, for determining at least one contaminated surface of the one or more surfaces 212, 214, 216, 218, and 220 when the at least one exposure characteristic does not exceed the threshold parameter. In an embodiment, the processor 302 determines that all surfaces 212, 214, 216, 218, and 220 of the device 104 are disinfected by performing the step 414. For example, when a measure of moisture content does not exceed a moisture threshold parameter, the processor 302 determines at least one contaminated surface, as described further in conjunction with FIG. 7. In another example, when a duration of application of a disinfecting agent does not exceed a time threshold parameter, the processor 302 determines the at least one contaminated surface, as described further in conjunction with FIG. 7. In another example, when a time duration between subsequent instances of application of a disinfecting agent on the one or more surfaces 212, 214, 216, 218, and 220 does not exceed a time interval threshold parameter, the processor 302 determines the at least one contaminated surface, as described further in conjunction with FIG. 8.

At step 416, the device 104 includes means such as, the processor 302 and/or the like, for generating a second notification to indicate that the at least one contaminated surface 212, 214, 216, 218, or 220 is not disinfected and requires disinfection by the disinfecting agent. In an embodiment, the second notification comprises, for example, a text message, an audio message, a vibration, a color-coded LED indicator, etc. The generation of the second notification based on the comparison of the measure of the moisture content and the first time duration with a moisture threshold parameter and a time threshold parameter, respectively, is further described in conjunction with FIG. 7. The generation of the second notification based on the comparison of the second time duration with a time interval threshold parameter is further described in conjunction with FIG. 8. The generation of the second notification based on the comparison of the chemical property of the disinfecting agent with a reference chemical property is described later in conjunction with FIG. 9.

In some examples, the processor 302 may not perform the steps 414 and 416 when none of the surfaces 212, 214, 216, 218, and 220 are contaminated.

In some examples, the scope of the disclosure is not limited to the device 104 generating the first notification and the second notification. In such an embodiment, after step 402, the device 104 includes means such as, the processor 302 and/or the like, for transmitting the sensor data to a processor 1002 of the server 108 (exemplarily illustrated in FIG. 10) via the network 106. The server 108 is configured to determine the at least one exposure characteristic and to generate the first notification or the second notification based on the comparison of the at least one exposure characteristic to the threshold parameter. In this embodiment, the device 104 includes means such as, the processor 302 and/or the like, for receiving the first notification and/or the second notification from the server 108, as further described in conjunction with FIG. 11.

Figure 5:
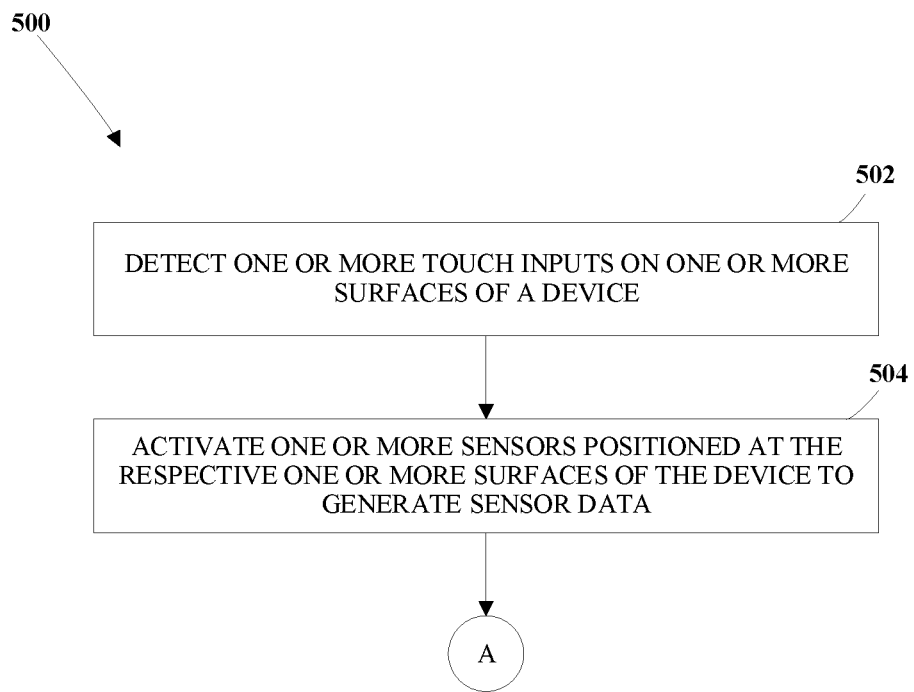
FIG. 5 illustrates a flowchart of a method for activating one or more sensors for monitoring the disinfection of the device, according to one or more embodiments described herein.

FIG. 5 illustrates a flowchart 500 of a method for activating one or more sensors 312, 314, 316, and 318 for monitoring the disinfection of the device 104, according to one or more embodiments described herein. At step 502, the device 104 includes means such as, the processor 302 and/or the like, for detecting one or more touch inputs on the one or more surfaces 212, 214, 216, 218, and 220 of the plurality of surfaces 212, 214, 216, 218, and 220 of the device 104. In an embodiment, the processor 302 receives signals from one or more sensors 312, 314, 316, and 318 of the plurality of sensors 312, 314, 316, and 318 comprising a plurality of capacitive touch sensors positioned at the respective plurality of surfaces 212, 214, 216, 218, and 220 of the device 104, for example, a front surface 212 comprising the display screen 110, a back surface 214, a side surface 216, a top surface 218, a bottom surface 220, etc. In an example embodiment, the reception of the signals may indicate the reception of the one or more touch inputs from the user 102 on the display screen 110, the back surface 214, the side surface 216, the top surface 218, the bottom surface 220, etc. Further, because the processor 302 receives the signals from the plurality of capacitive touch sensors, the plurality of touch sensors may have received the one or more touch inputs.

In an embodiment, the processor 302 determines a location of the plurality of touch sensors on the display screen 110, the back surface 214, the side surface 216, the top surface 218, the bottom surface 220, etc., of the device 104. In an embodiment, the memory unit 304 includes data pertaining to the plurality of touch sensors. The data includes location information of the plurality of touch sensors and a respective unique address associated with each touch sensor of the plurality of sensors 312, 314, 316, and 318. In an example embodiment, based on the reception of the signals, the processor 302 may be configured to uniquely identify the plurality of touch sensors of the plurality of touch sensors that has received the one or more touch inputs. Thereafter, the processor 302 may be configured to determine the location of the plurality of touch sensors on the device 104 from the data pertaining to the plurality of touch sensors stored in the memory unit 304.

At step 504, the device 104 includes means such as, the processor 302 and/or the like, for activating one or more sensors 312, 314, 316, and 318 of the plurality of sensors 312, 314, 316, and 318 positioned at the respective one or more surfaces 212, 214, 216, 218, and 220 of the device 104 to generate the sensor data. After the identification of the locations of the touch sensors (which have received the one or more touch inputs), the processor 302 may be configured to activate the one or more sensors 312, 314, 316, and 318 of the plurality of sensors 312, 314, 316, and 318 positioned at the identified locations. The activated one or more sensors 312, 314, 316, and 318 are configured to generate the sensor data. The generated sensor data may then be used by the device 104 including means such as, the processor 302, and/or the like, for monitoring disinfection of the device 104, as described in conjunction with FIGS. 7-9. In some examples, the scope of the disclosure is not limited to the activation of the one or more sensors of the plurality of sensors 312, 314, 316, and 318 based on the reception of the touch input, the one or more sensors may be always activated.

Figure 6:
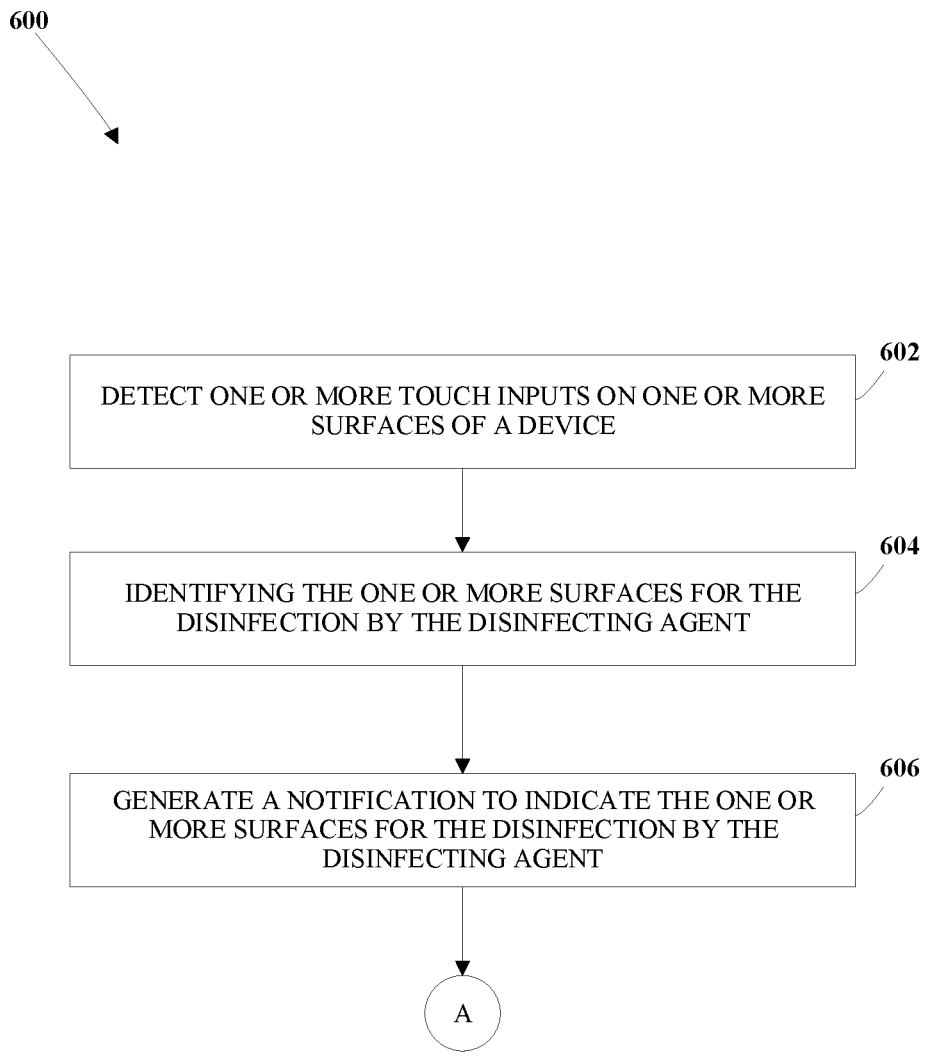
FIG. 6 illustrates a flowchart of a method for identifying one or more surfaces of the device for disinfection by the disinfecting agent, according to one or more embodiments described herein.

FIG. 6 illustrates a flowchart 600 of a method for identifying one or more surfaces 212, 214, 216, 218, and 220 of the device 104 for disinfection by the disinfecting agent, according to one or more embodiments described herein.

At step 602, the device 104 includes means such as, the processor 302, and/or the like, for detecting one or more touch inputs on one or more surfaces 212, 214, 216, 218, and 220 of the device 104. In an embodiment, the processor 302 receives signals from a set of touch sensors of the plurality of sensors 312, 314, 316, and 318 positioned at the respective plurality of surfaces 212, 214, 216, 218, and 220 of the device 104, for example, a front surface 212 comprising the display screen 110, a back surface 214 of the device 104, a side surface 216 of the device 104, a top surface 218 of the device 104, a bottom surface 220 of the device 104, etc. In an example embodiment, the reception of the signals may indicate the reception of the one or more touch inputs from the user 102 on the display screen 110, the back surface 214, the side surface 216, the top surface 218, the bottom surface 220, etc. Further, because the processor 302 receives the signals from the set of touch sensors, the set of touch sensors may have received the one or more touch inputs.

At step 604, the device 104 includes means such as, the processor 302, and/or the like, for identifying the one or more surfaces 212, 214, 216, 218, and 220 for the disinfection by the disinfecting agent, based on the one or more touch inputs. In an embodiment, the processor 302 determines a location of the set of touch sensors on the display screen 110, the back surface 214, the side surface 216, the top surface 218, the bottom surface 220, etc., of the device 104. In an embodiment, the memory unit 304 includes data pertaining to the plurality of touch sensors. The data includes location information of the plurality of touch sensors and a respective unique address associated with each touch sensor of the plurality of sensors 312, 314, 316, and 318. In an example embodiment, based on the reception of the signals, the processor 302 may be configured to uniquely identify the set of touch sensors of the plurality of touch sensors that has received the one or more touch inputs. Thereafter, the processor 302 may be configured to determine locations of the set of touch sensors on the device 104 from the data pertaining to the plurality of touch sensors stored in the memory unit 304, as described in conjunction with FIG. 5.

At step 606, the device 104 includes means such as, the processor 302, and/or the like, for generating a notification to indicate the one or more surfaces 212, 214, 216, 218, and 220 for the disinfection by the disinfecting agent. The notification may comprise, for example, a text message, an audio message, a vibration, a color-coded LED indicator, etc. The user 102 may receive the notification via the user interface 308 of the device 104 and apply the disinfecting agent on the one or more surfaces 212, 214, 216, 218, and 220 of the device 104 as indicated in the notification.

In an embodiment, the device 104 includes means such as, the processor 302, and/or the like, for receiving the sensor data from the plurality of sensors 312, 314, 316, and 318 positioned at the respective one or more surfaces 212, 214, 216, 218, and 220 of the device 104. The sensor data may then be used by the device 104 including means such as, the processor 302, and/or the like, for monitoring disinfection of the device 104, as described in conjunction with FIGS. 7-9.

Figure 7:
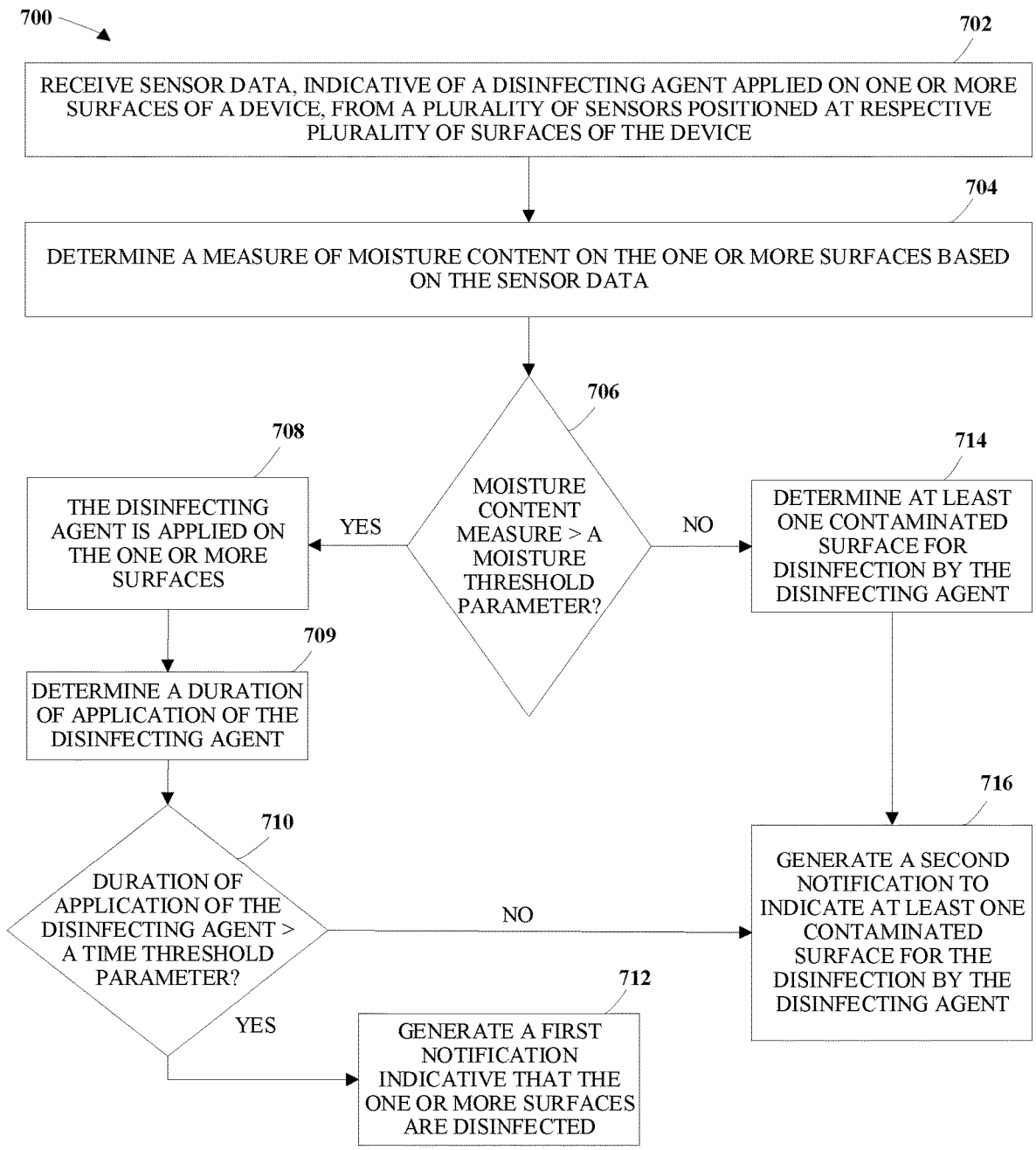
FIG. 7 illustrates a flowchart of a method for monitoring the disinfection of the device based on moisture content on the device, according to one or more embodiments described herein.

FIG. 7 illustrates a flowchart 700 of a method for monitoring the disinfection of the device 104 based on determination of a measure of moisture content on the device 104, according to one or more embodiments described herein. At step 702, the device 104 includes means such as, the processor 302 and/or the like, for receiving the sensor data from the plurality of sensors 312, 314, 316, and 318. As discussed in conjunction with FIG. 3, the plurality of sensors 312, 314, 316, and 318 may correspond to for example, touch sensors, light sensors, and/or the like.

At step 704, the device 104 includes means such as, the processor 302 and/or the like, for determining the measure of moisture content on the one or more surfaces 212, 214, 216, 218, and 220 based on the sensor data. In an embodiment, the processor 302 receives sensor data comprising a plurality of touch signals from a plurality of sensors 312, 314, 316, and 318 comprising, for example, touch sensors to determine the measure of moisture content on the one or more surfaces 212, 214, 216, 218, and 220, as discussed in conjunction with FIG. 3.

In this embodiment, changes in capacitance values of a surface, for example, the front surface 212 comprising the display screen 110 of the device 104, may be due to moisture accumulation on the surface 212. Because the capacitance value of the surface 212 varies upon moisture accumulation, therefore, by monitoring the changes in the capacitance values, the measure of moisture content on the display screen 110 of the device 104 may be detected, as described in conjunction with FIG. 3. Similarly, in another embodiment, by monitoring the changes in the capacitance values of other surfaces 214, 216, 218, and 220 of the device 104 such as the back surface 214, the side surface 216, the top surface 218, the bottom surface 220 (exemplarily illustrated in FIG. 2), the measure of moisture content on the other surfaces 214, 216, 218, and 220 of the device 104 may be detected.

At step 706, the device 104 includes means such as, the processor 302 and/or the like, for determining whether the measure of moisture content exceeds a moisture threshold parameter. As used herein, the phrase "moisture threshold parameter" may refer to a quantitative value of moisture content attributed by a disinfecting agent on a surface 212, 214, 216, 218, or 220 of the device 104, below which the surface 212, 214, 216, 218, or 220 of the device 104 is deemed to be contaminated. In an example embodiment, the moisture threshold parameter is determined by the server 108, as described further in conjunction with FIG. 13. In an embodiment, the moisture content on the surface 212, 214, 216, 218, or 220 is measured by a sensor 312, 314, 316, or 318 such as a touch sensor that detects a change in capacitance of the surface 212, 214, 216, 218, or 220.

At step 708, the device 104 includes means such as, the processor 302 and/or the like, for determining that the disinfecting agent is applied on the one or more surfaces 212, 214, 216, 218, and 220 when the measure of moisture content exceeds the moisture threshold parameter. In an example embodiment, if a user 102 is trying to cheat the process of determining disinfection by touching few areas of the surface 212, 214, 216, 218, or 220 with wet fingers, only the sensors 312, 314, 316, and 318 (for example, touch sensors) corresponding to the areas of the surface 212, 214, 216, 218, or 220 that are touched by the wet fingers may detect the moisture content while the rest of the sensors 312, 314, 316, and 318 corresponding to areas of the rest of the surface 212, 214, 216, 218, or 220 that remains dry may not detect the moisture content. Accordingly, since electrical signals generated by each sensor 312, 314, 316, and 318 differs based on each surface 212, 214, 216, 218, or 220 of the plurality of surfaces being wet or dry, the processor 302 uses the sensor data from each of the sensors 312, 314, 316, and 318 to differentiate between areas of the surface 212, 214, 216, 218, or 220 that are wiped with the disinfecting agent and areas of the surface 212, 214, 216, 218, or 220 that are touched with the wet fingers. Accordingly, the processor 302 ensures error-free determination of disinfected and/or contaminated surfaces 212, 214, 216, 218, or 220 of the device 104.

In response to determining that the disinfecting agent is applied on the one or more surfaces 212, 214, 216, 218, and 220, at step 709, the device 104 includes means such as, the processor 302 and/or the like, for determining a time duration associated with application of the disinfecting agent on the one or more surfaces 212, 214, 216, 218, and 220 of the device 104. For example, the processor 302 receives time data from a timer of the device 104 communicatively coupled to the processor 302. Based on the time data from the timer, the processor 302 determines the time duration associated with application of the disinfecting agent on the one or more surfaces 212, 214, 216, 218, and 220 of the device 104.

At step 710, the device 104 includes means such as, the processor 302 and/or the like, for determining whether the time duration associated with application of the disinfecting agent on the one or more surfaces 212, 214, 216, 218, and 220 exceeds a time threshold parameter. As used herein, the phrase "time threshold parameter" may refer to a temporal value of time duration, such as evaporation rate, associated with application of the disinfecting agent below which a surface 212, 214, 216, 218, or 220 of the device 104 is deemed to be contaminated. In an example embodiment, the time threshold parameter is determined by the server 108, as described further in conjunction with FIG. 13. By performing the step 710, the processor 302 checks whether the measure of moisture content is greater than the moisture threshold parameter for a predetermined time duration. Accordingly, by performing the step 710, the processor 302 avoids false determination of the measure of moisture content being greater than the moisture threshold parameter. For example, on application of the disinfecting agent on a surface 212, 214, 216, 218, or 220 of the device 104, the capacitance value in a first time duration t1 satisfies (e.g. is greater than) the moisture threshold parameter. However, during a subsequent instance of application of the disinfecting agent, a second time duration t2 associated with the application of the disinfecting agent does not satisfy (e.g., less than) the time threshold parameter. Therefore, had the processor 302 not performed the step 710, the processor 302 would have, incorrectly, performed the step 712.

At step 712, in response to the determining that the time duration associated with application of the disinfecting agent exceeds the time threshold parameter, the device 104 includes means such as, the processor 302 and/or the like, for generating the first notification to indicate that the one or more surfaces 212, 214, 216, 218, and 220 are disinfected. The first notification comprises, for example, a text message, an audio message, a vibration, a color-coded LED indicator, etc.

At step 714, the device 104 includes means such as, the processor 302 and/or the like, for determining at least one contaminated surface of the one or more surfaces 212, 214, 216, 218, and 220 when the time duration associated with application of the disinfecting agent does not exceed the time threshold parameter. For example, the time threshold parameter may indicate that the disinfecting agent may be applied for 20 seconds on a surface, for example, 212. However, the processor 302 determines that the disinfecting agent is applied for 15 seconds on the surface 212. Accordingly, the processor 302 determines the surface 212 as the at least one contaminated surface. In an embodiment, the at least one contaminated surface may correspond to one contaminated surface 212, 214, 216, 218, or 220 or all contaminated surfaces 212, 214, 216, 218, and 220 of the device 104. At step 716, in response to the determining that at least one contaminated surface, the device 104 includes means such as, the processor 302 and/or the like, for generating the second notification to indicate the at least one contaminated surface of the one or more surfaces 212, 214, 216, 218, and 220 for disinfection by the disinfecting agent. The second notification comprises, for example, a text message, an audio message, a vibration, a color-coded LED indicator, etc. Further, at step 716, in response to the determining that the time duration associated with application of the disinfecting agent does not exceed the time threshold parameter, the device 104 includes means such as, the processor 302 and/or the like, for generating the second notification to indicate the at least one contaminated surface of the one or more surfaces 212, 214, 216, 218, and 220 for disinfection by the disinfecting agent.

Figure 8:
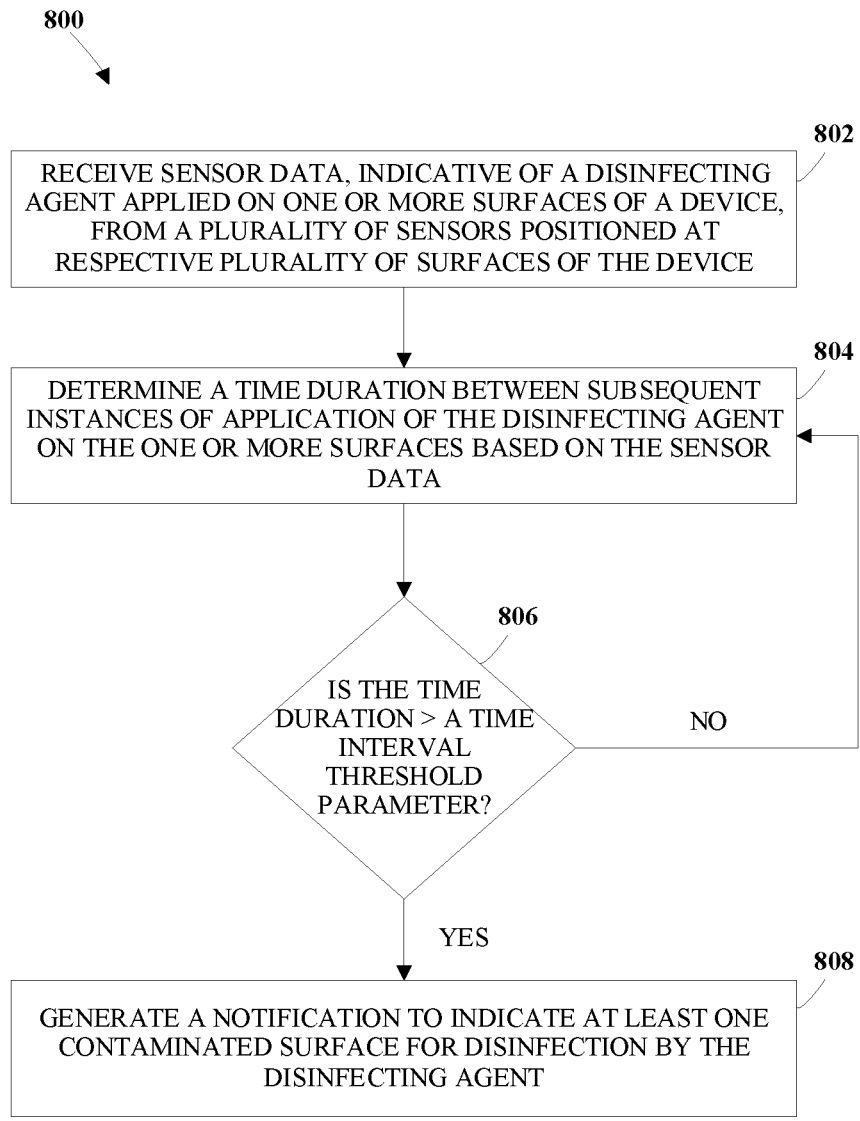
FIG. 8 illustrates a flowchart of a method for monitoring the disinfection of the device based on a time duration between subsequent instances of the disinfection of the device, according to one or more embodiments described herein.

FIG. 8 illustrates a flowchart 800 of a method for monitoring disinfection of the device 104 based on a time duration between subsequent instances of application of the disinfecting agent on the one or more surfaces 212, 214, 216, 218, and 220 of the device 104, according to one or more embodiments described herein.

At step 802, the device 104 includes means such as, the processor 302 and/or the like, for receiving the sensor data from the plurality of sensors 312, 314, 316, and 318. As discussed, in conjunction with FIG. 3, the plurality of sensors 312, 314, 316, and 318 may correspond to, for example, touch sensors, light sensors, and/or the like.

At step 804, the device 104 includes means such as, the processor 302 and/or the like, for determining a time duration between subsequent instances of application of the disinfecting agent on the one or more surfaces 212, 214, 216, 218, and 220 of the device 104, based on the sensor data. For example, the processor 302 determines a first time instance at which a first measure of moisture content is determined to satisfy (e.g. is greater than) the moisture threshold parameter, as described in conjunction with FIG. 7. In an embodiment, the processor 302 receives time data from the timer of the device 104 communicatively coupled to the processor 302. Based on the time data from the timer, the processor 302 determines the time duration that has elapsed between the subsequent instances of application of the disinfecting agent exceeds time interval threshold parameter. Further, the processor 302 determines a second time instance at which a second measure of moisture content is determined to satisfy (e.g. is greater than) the moisture threshold parameter, as described in conjunction with FIG. 7. Further, the processor 302 determines a time duration that has elapsed between the first time instance and the second time instance to determine the time duration between subsequent instances of application of the disinfecting agent on the one or more surfaces 212, 214, 216, 218, and 220 of the device 104. For example, the processor 302 receives time data from a timer of the device 104 communicatively coupled to the processor 302. Based on the time data from the timer, the processor 302 determines the time duration that has elapsed between the first time instance and the second time instance.

At step 806, the device 104 includes means such as, the processor 302 and/or the like, for determining whether the time duration exceeds a time interval threshold parameter. As used herein, the phrase "time interval threshold parameter" refers to a temporal value of a time interval between subsequent instances of application of the disinfecting agent on a surface 212, 214, 216, 218, or 220 above which the surface 212, 214, 216, 218, or 220 of the device 104 is deemed to be contaminated or corresponds to a delay in disinfection of the surface 212, 214, 216, 218, or 220 of the device 104. In an example embodiment, the time interval threshold parameter is determined by the server 108, as described further in conjunction with FIG. 13. Based on the time data from the timer, the processor 302 determines the time duration that has elapsed between the subsequent instances of application of the disinfecting agent exceeds time interval threshold parameter. Accordingly, the processor 302 determines that the surface 212, 214, 216, 218, or 220 is contaminated when the time duration between the subsequent instances of application of the disinfecting agent exceeds the time interval threshold parameter, due to lack of disinfection by the disinfecting agent in that time duration. The processor 302 determines that the surface 212, 214, 216, 218, or 220 is not contaminated when the time duration between the subsequent instances of application of the disinfecting agent does not exceed the time interval threshold parameter.

At step 808, the device 104 includes means such as, the processor 302 and/or the like, for generating the second notification to indicate the at least one contaminated surface 212, 214, 216, 218, or 220 for disinfection by the disinfecting agent, when the time duration exceeds the time interval threshold parameter. In an embodiment, the at least one contaminated surface may correspond to one contaminated surface 212, 214, 216, 218, or 220 or all contaminated surfaces 212, 214, 216, 218, and 220 of the device 104. When the time duration does not exceed the time interval threshold parameter, the device 104 includes means such as, the processor 302 and/or the like, to repeat the step 804.

Figure 9:
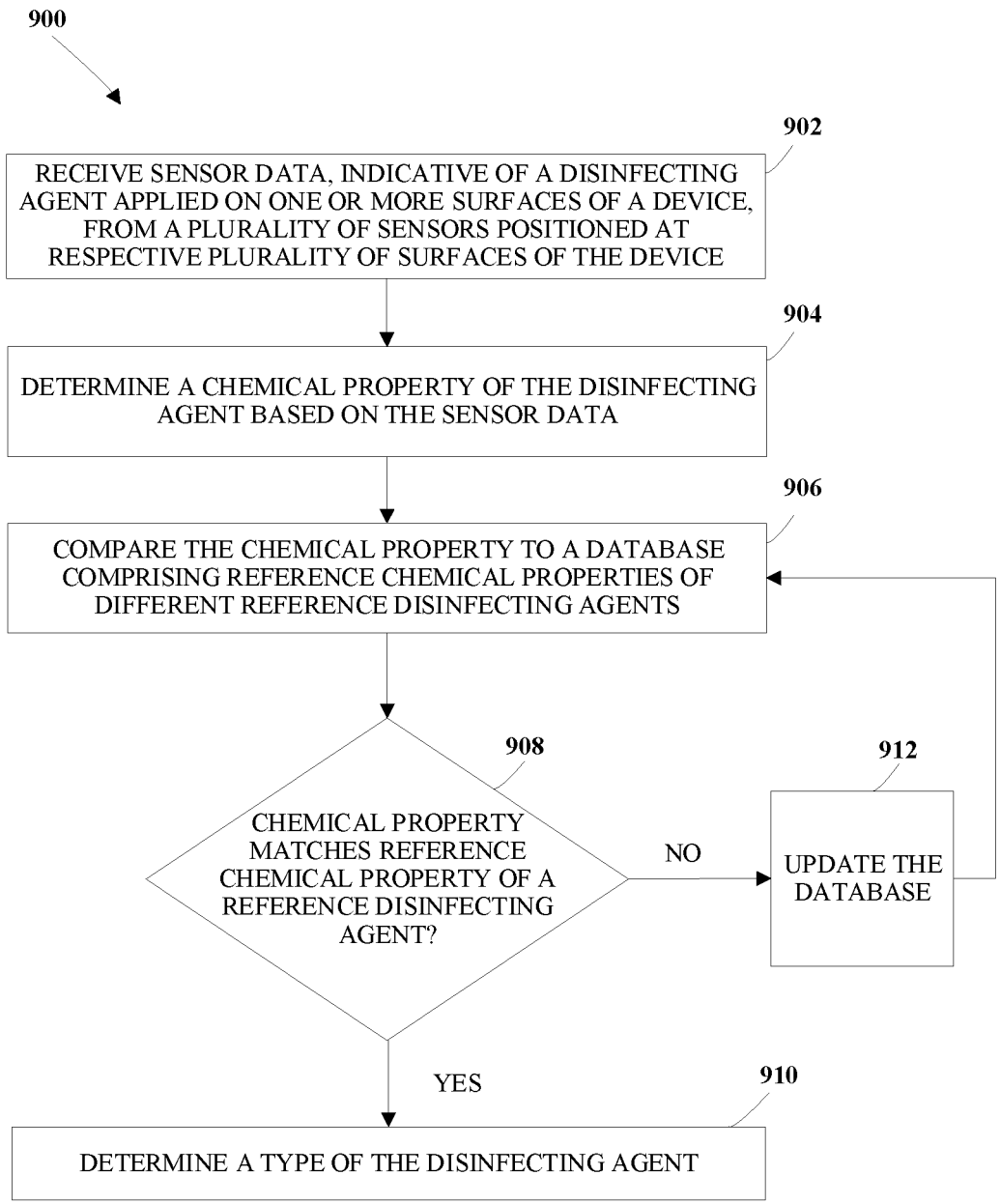
FIG. 9 illustrates a flowchart of a method for monitoring disinfection of the device based on a type of the disinfecting agent, according to one or more embodiments described herein.

FIG. 9 illustrates a flowchart 900 of a method for monitoring disinfection of the device 104 based on a type of the disinfecting agent applied on the one or more surfaces 212, 214, 216, 218, and 220 of the device 104, according to one or more embodiments described herein.

At step 902, the device 104 includes means such as, the processor 302 and/or the like, for receiving the sensor data from the plurality of sensors 312, 314, 316, and 318. As discussed, in conjunction with FIG. 3, the plurality of sensors 312, 314, 316, and 318 may correspond to, for example, touch sensors, light sensors, and/or the like.

At step 904, the device 104 includes means such as, the processor 302 and/or the like, for determining a chemical property of the disinfecting agent. In an embodiment, the chemical property corresponds to an evaporation rate of the disinfecting agent. In another embodiment, the chemical property is not limited to the evaporation rate and may comprise, for example, alcohol concentration, viscosity, surface tension, critical temperature, critical pressure, etc. In an embodiment, the processor 302 determines the chemical property based on the sensor data generated by the one or more sensors of the plurality of sensors 312, 314, 316, and 318. For example, the sensor data of the plurality of sensors 312, 314, 316, and 318 comprising, for example, touch sensors on the display screen 110 indicate a change in capacitance at a particular location on the display screen 110 that corresponds to a touch input such as, a disinfecting agent wiped with a wiping cloth. As moisture caused by the disinfecting agent evaporates from the surface 212 of the display screen 110, the capacitance changes. The processor 302 detects the rate of change of the capacitance corresponding to the display screen 110 to determine the evaporation rate of the disinfecting agent.

At step 906, the device 104 includes means such as, the processor 302 and/or the like, for comparing the chemical property to a database comprising reference chemical properties of different reference disinfecting agents. As used herein, the phrase "reference chemical properties" refers to chemical properties such as evaporation rates of different reference disinfecting agents such as alcohol, organic acids, oxidizing agents, etc. For example, the processor 302 compares the determined evaporation rate of the disinfecting agent with respective evaporation rates of different reference disinfecting agents stored in the database. At step 908, the device 104 includes means such as, the processor 302 and/or the like, for determining whether the chemical property of the disinfecting agent matches a reference chemical property of any reference disinfecting agent stored in the database. For example, the processor 302 determines whether the evaporation rate of the disinfecting agent matches a reference evaporation rate of a reference disinfecting agent such as, water, ethanol, isopropanol, peroxide, hydrogen peroxide, caprylic acid, citric acid, lactic acid, etc.

At step 910, the device 104 includes means such as, the processor 302 and/or the like, for determining a type of the disinfecting agent when the chemical property of the disinfecting agent matches the reference chemical property of the reference disinfecting agent stored in the database. The disinfecting agent may refer to a cleaning solution that is used to kill microorganisms such as bacteria, fungi, viruses, etc., present on a contaminated surface, such as surface 212, 214, 216, 218, or 220 of a device 104. In an embodiment, the disinfecting agent may correspond to a solution comprising, for example, water, alcohol such as ethanol, isopropanol, peroxide, hydrogen peroxide, caprylic acid, citric acid, lactic acid, etc. In an example embodiment, the disinfecting agent corresponds to a solution comprising 70% isopropyl alcohol. In an embodiment, a disinfecting agent is categorized based on chemical components of the disinfecting agent. For example, various types of disinfecting agents correspond to, but not limited to, alcoholic disinfectants such as ethanol, isopropanol, etc., oxidizing disinfectants such as peroxide, hydrogen peroxide, etc., organic acids such as caprylic acid, citric acid, lactic acid, etc. In an embodiment, the disinfecting agent may also refer to water. For example, when the evaporation rate of the disinfecting agent matches a reference evaporation rate of ethanol, the processor 302 determines that a type of the disinfecting agent is an alcohol. At step 912, the device 104 includes means such as, the processor 302 and/or the like, for updating the database when the chemical property of the disinfecting agent does not match the reference chemical property of any reference disinfecting agent stored in the database. For example, when the processor 302 does not find a match for the chemical property of the disinfecting agent with a reference chemical property of a reference disinfecting agent in the database, the processor 302 updates the database with data corresponding to the disinfecting agent using conventional online analytical processing (OLAP) and data mining techniques. In an embodiment, the processor 302 updates the database using conventional online analytical processing (OLAP) and data mining techniques. When the database is updated, the device 104 includes means such as, the processor 302 and/or the like, to repeat the step 906.

Figure 10:
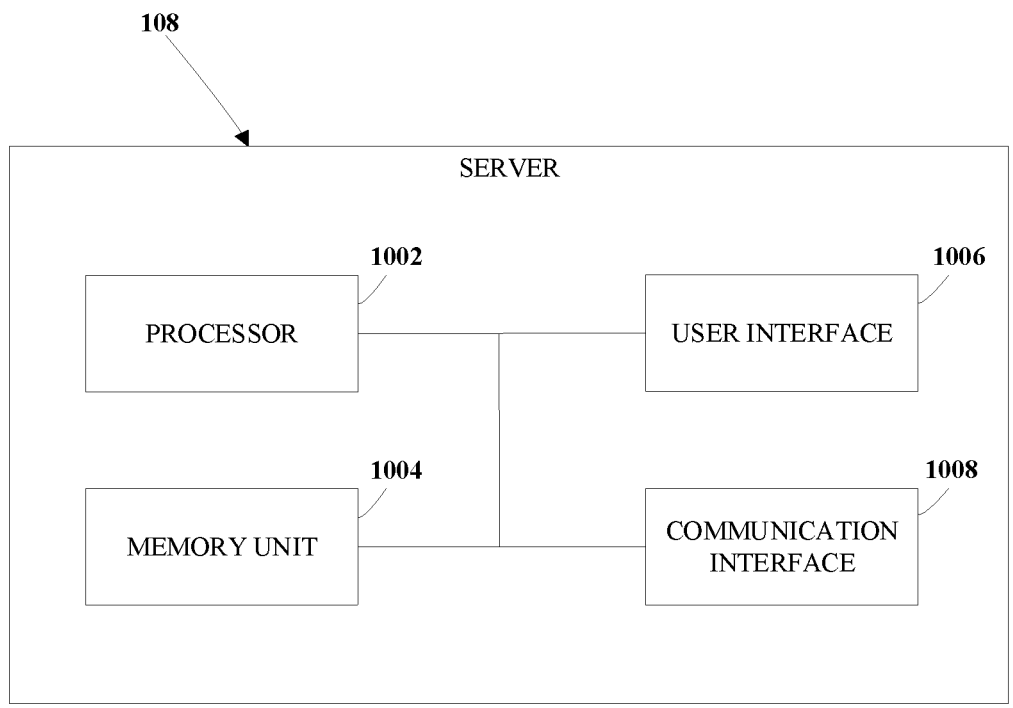
FIG. 10 illustrates a block diagram of a server, according to one or more embodiments described herein.

FIG. 10 illustrates a block diagram of the server 108, according to one or more embodiments described herein. The server 108 comprises a processor 1002, a memory unit 1004, a user interface 1006, a communication interface 1008, as exemplarily illustrated in FIG. 10.

The processor 1002 may be embodied as means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 10 as a single processor 1002, in an embodiment, the processor 1002 may include a plurality of processors and signal processing modules. The plurality of processors may be embodied on a single server 108 or may be distributed across a plurality of servers 108 collectively configured to function as the circuitry of the server 108. The plurality of processors may be in operative communication with each other and may be collectively configured to perform one or more functionalities of the circuitry of the server 108, as described herein. In an example embodiment, the processor 1002 may be configured to execute instructions stored in the memory unit 1004 or otherwise accessible to the processor 1002. These instructions, when executed by the processor 1002, may cause the circuitry of the server 108 to perform one or more of the functionalities, as described herein.

Whether configured by hardware, firmware/software methods, or by a combination thereof, the processor 1002 may include an entity capable of performing operations according to embodiments of the present disclosure while configured accordingly. Thus, for example, when the processor 1002 is embodied as an ASIC, FPGA or the like, the processor 1002 may include specifically configured hardware for conducting one or more operations described herein. Alternatively, as another example, when the processor 1002 is embodied as an executor of instructions, such as may be stored in the memory unit 1004, the instructions may specifically configure the processor 1002 to perform one or more algorithms and operations described herein.

Thus, the processor 1002 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor 1002 dedicated to running other applications. Software applications may be stored in the memory unit 1004 before they are accessed and loaded into the processors. The processors may include internal memory sufficient to store the application software instructions. In many devices, the memory unit 1004 may be a volatile or nonvolatile memory, such as flash memory, or a mixture of both. The memory unit 1004 can also be located internal to another computing resource (e.g., enabling computer readable instructions to be downloaded over the Internet or another wired or wireless connection).

In an example embodiment, the processor 1002 may be configured to be communicatively coupled to the device 104 via the network 106. The processor 1002 is configured to receive, from the device 104, sensor data from a plurality of sensors 312, 314, 316, and 318 (exemplarily illustrated in FIG. 3) positioned at a respective plurality of surfaces 212, 214, 216, 218, and 220 of the device 104. The sensor data indicates that a disinfecting agent is applied on one or more surfaces 212, 214, 216, 218, and 220 of the plurality of surfaces 212, 214, 216, 218, and 220 of the device 104.

In an embodiment, purr to receiving the sensor data, the processor 1002 may be configured to receive data associated with one or more touch inputs on one or more surfaces 212, 214, 216, 218, and 220 of a plurality of surfaces 212, 214, 216, 218, and 220 of the device 104. In response to receiving the data, the processor 1002 may be configured to identify the one or more surfaces 212, 214, 216, 218, and 220 of the device 104 for disinfection by the disinfecting agent. The processor 1002 may be further configured to generate a notification to indicate the one or more surfaces 212, 214, 216, 218, and 220 for the disinfection by the disinfecting agent. The processor 1002 may be further configured to transmit the notification to the device 104 via the network 106. This embodiment is further described in conjunction with FIG. 11.

In an embodiment, the processor 1002 may be configured to receive the sensor data from the plurality of sensors 312, 314, 316, and 318. The processor 1002 may be configured to determine at least one exposure characteristic based on the sensor data. The at least one exposure characteristic is associated with disinfection of the one or more surfaces 212, 214, 216, 218, and 220 of the device 104 by the disinfecting agent. The processor 1002 may be configured to compare the at least one exposure characteristic to a threshold parameter associated with the at least one exposure characteristic. In response to the comparison, the processor 1002 may be configured to generate a first notification indicating that the one or more surfaces 212, 214, 216, 218, and 220 of the device 104 are disinfected. The processor 1002 may be configured to transmit the first notification to the device 104 via the network 106. Further, in response to the comparison, the processor 1002 may be configured to determine at least one contaminated surface 212, 214, 216, 218, and 220 of the one or more surfaces 212, 214, 216, 218, and 220 when the at least one exposure characteristic is below the threshold parameter. The processor 1002 may be configured to generate a second notification to indicate the at least one contaminated surface 212, 214, 216, 218, and 220 for the disinfection by the disinfecting agent. The processor 1002 may be configured to transmit the second notification to the device 104 via the network 106. This embodiment is further described in conjunction with FIG. 11.

In an embodiment, the at least one exposure characteristic comprises a measure of moisture content on the one or more surfaces 212, 214, 216, 218, and 220 of the device 104, a first time duration associated with application of the disinfecting agent on the one or more surfaces 212, 214, 216, 218, and 220 of the device 104, a second time duration between subsequent instances of application of the disinfecting agent on the one or more surfaces 212, 214, 216, 218, and 220 of the device 104, and/or a chemical property of the disinfecting agent. In an embodiment, the processor 1002 may be further configured to monitor disinfection of the device 104 based on comparison of the measure of moisture content to a moisture threshold parameter, as further described in conjunction with FIG. 12. In an embodiment, the processor 1002 may be further configured to monitor disinfection of the device 104 based on comparison of the first time duration associated with application of the disinfecting agent on the one or more surfaces 212, 214, 216, 218, and 220 of the device 104 to a time threshold parameter, as further described in conjunction with FIG. 12. In an embodiment, the processor 1002 may be further configured to monitor disinfection of the device 104 based on comparison of the second time duration between subsequent instances of application of the disinfecting agent on the one or more surfaces 212, 214, 216, 218, and 220 of the device 104 to a time interval threshold parameter, as further described in conjunction with FIG. 8. In an embodiment, the processor 1002 may be further configured to determine a type of the disinfecting agent based on comparison of the chemical property to a reference chemical property stored in a database, as further described in conjunction with FIG. 9.

The memory unit 1004 may include suitable logic, circuitry, and/or interfaces that are adapted to store a set of instructions that is executable by the processor 1002 to perform predetermined operations. Software applications may be stored in the memory unit 1004 before they are accessed and loaded into the processor 1002. The processor 1002 may include internal memory sufficient to store the application software instructions. In many devices, the memory unit 1004 may be a volatile or nonvolatile memory, such as flash memory, or a mixture of both. The memory unit 1004 can also be located internal to another computing resource (e.g., enabling computer readable instructions to be downloaded over the Internet or another wired or wireless connection). Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof In an embodiment, the memory unit 1004 may be integrated with the processor 1002 on a single chip, without departing from the scope of the disclosure. In an example embodiment, the memory unit 1004 may be configured to store data pertaining to the plurality of sensors 312, 314, 316, and 318 comprising, for example, the plurality of touch sensors. In an example embodiment, the data pertaining to the plurality of sensors 312, 314, 316, and 318 may include, but not limited to, a location of each sensor 312, 314, 316, and 318. In an example embodiment, the data pertaining to the plurality of touch sensors may include, but not limited to, a location of each touch sensor of the plurality of touch sensors. Further, the data includes unique address associated with each sensor 312, 314, 316, and 318 comprising, for example, touch sensors. In an example embodiment, the unique address may enable the processor 1002 to individually control the plurality of sensors 312, 314, 316, and 318. For example, based on the unique address, the processor 1002 may be able to uniquely identify which of the plurality of sensors 312, 314, 316, and 318 has sent an electrical signal (corresponding to the sensor data) to the processor 1002, or uniquely identify which of the plurality of touch sensors has sent the haptic signal (corresponding to the detected touch input) to the processor 1002.

The user interface 1006 may include suitable logic or circuitry that may enable the user interface 1006 to communicate with the device 104 via the network 106. The user interface 1006 may be implemented using one or more technologies, such as, but not limited to, FPGA, ASIC, and the like.

The communication interface 1008 may facilitate transmission and reception of messages and data to and from various components of the server 108. For example, the communication interface 1008 is communicatively coupled with the processor 1002, the memory unit 1004, and the user interface 1006. Examples of the communication interface 1008 may include, but are not limited to, an antenna, an Ethernet port, a USB port, a serial port, or any other port that can be adapted to receive and transmit data. The communication interface 1008 transmits and receives data and/or messages in accordance with the various communication protocols, such as, I2C, TCP/IP, UDP, 2G, 3G, 4G or 5G communication protocols, etc.

Figure 11:
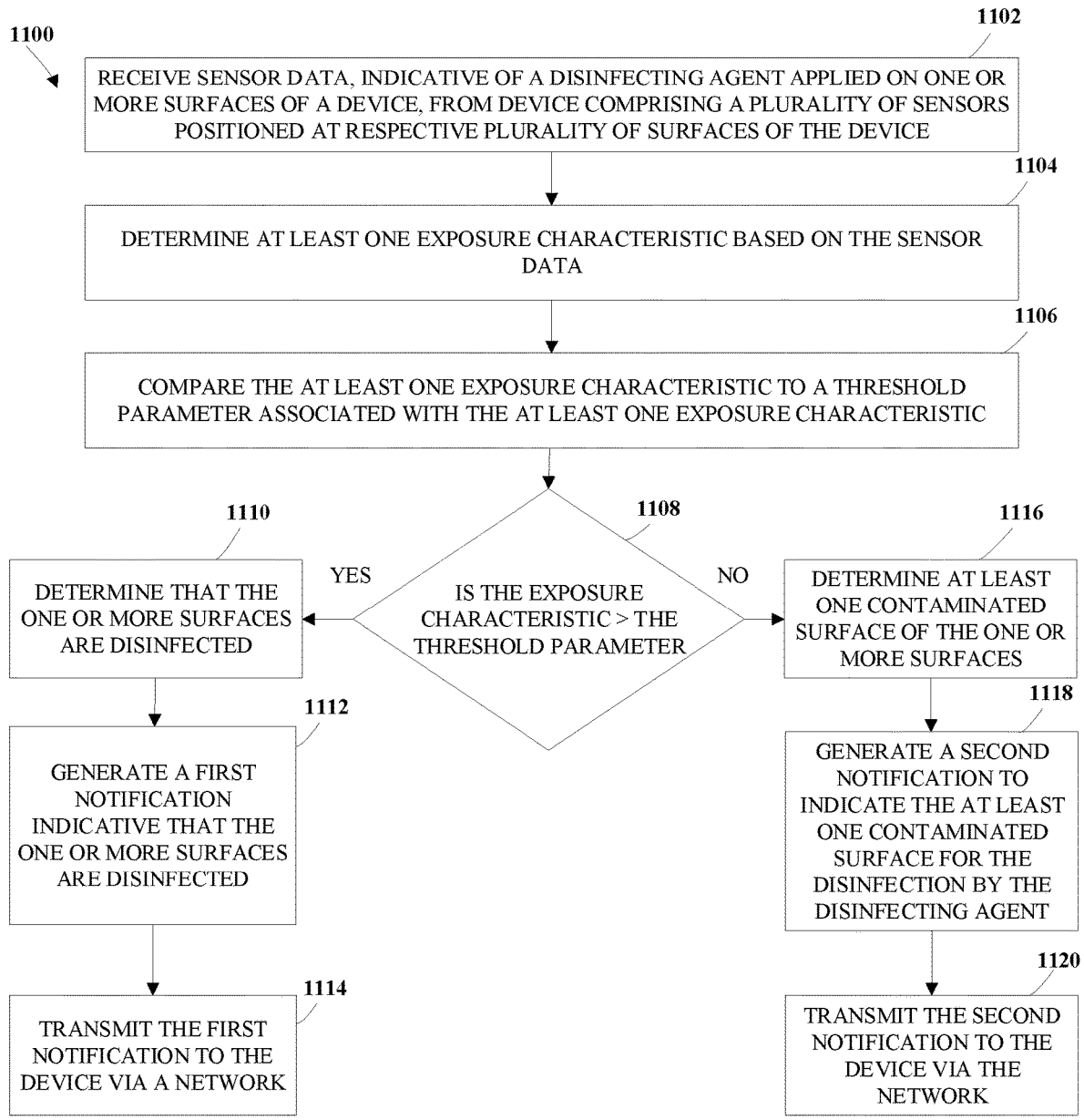
FIG. 11 illustrates a flowchart of a method performed by the server for monitoring disinfection of the device, according to one or more embodiments described herein.
Figure 12:
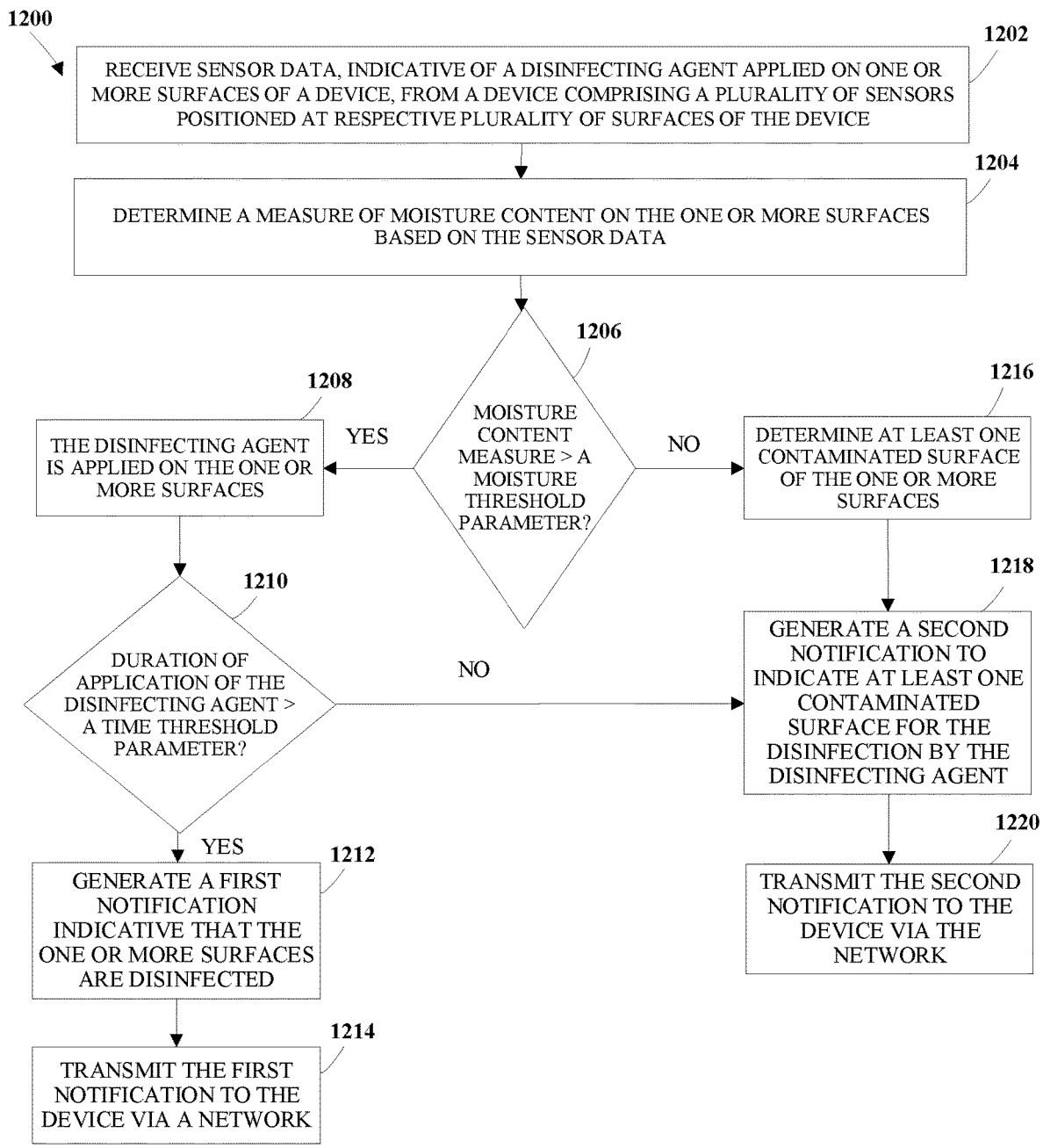
FIG. 12 illustrates a flowchart of a method performed by the server for monitoring the disinfection of the device based on moisture content on the device, according to one or more embodiments described herein.
Figure 13:
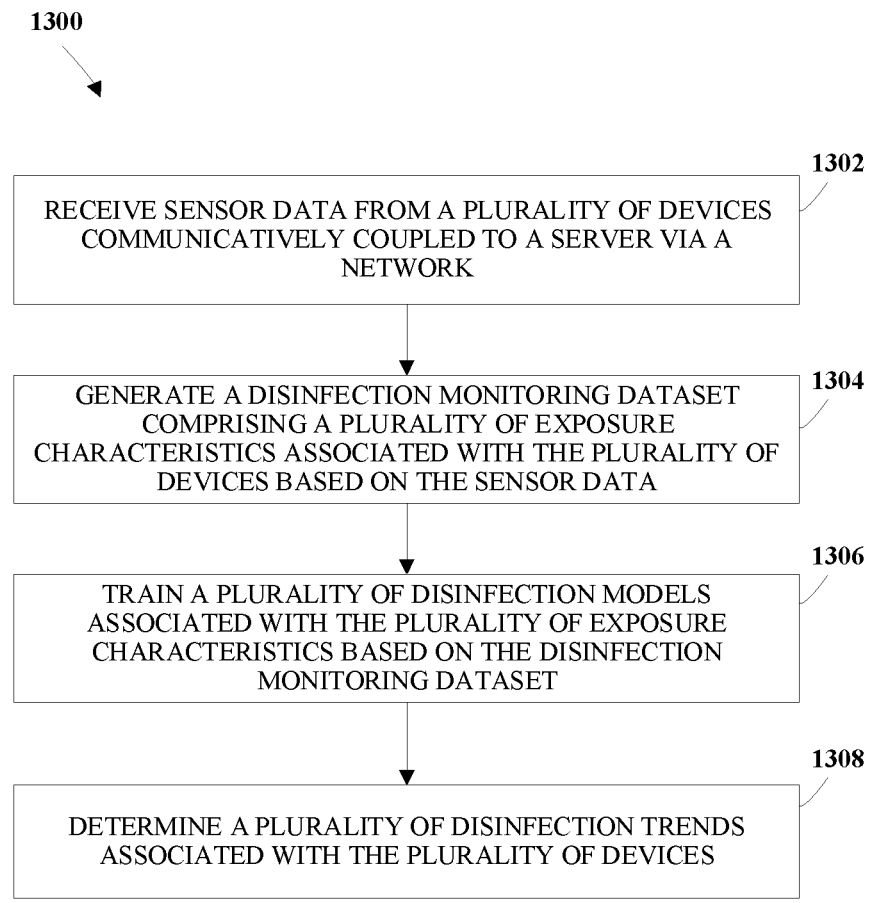
FIG. 13 illustrates a flowchart of a method performed by the server for generating disinfection models for monitoring the disinfection of the device, according to one or more embodiments described herein.

FIGS. 11-13 illustrate example flowcharts 1100, 1200, and 1300 of the operations performed by the server 108 of FIG. 10, in accordance with example embodiments of the present invention. It will be understood that each block of the flowcharts 1100, 1200, and 1300, and combinations of blocks in the flowcharts 1100, 1200, and 1300, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by the memory unit 1004 of the server 108 employing an embodiment of the present invention and executed by the processor 1002 in the server 108. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 11-13, when executed, convert a computer or processing circuitry into a particular machine configured to perform an example embodiment of the present invention. Accordingly, the operations of FIGS. 11-13 define an algorithm for configuring a computer or a processor, to perform an example embodiment. In some cases, a general-purpose computer may be provided with an instance of the processor 1002 which performs the algorithm of FIGS. 11-13 to transform the general-purpose computer into a particular machine configured to perform an example embodiment.

Accordingly, blocks of the flowchart support combinations of means for performing the specified functions and combinations of operations for performing the specified functions. It will also be understood that one or more blocks of the flowcharts 1100, 1200, and 1300, and combinations of blocks in the flowcharts 1100, 1200, and 1300, can be implemented by special purpose hardware-based computer systems which perform the specified functions, or combinations of special purpose hardware and computer instructions.

FIG. 11 illustrates a flowchart 1100 of a method performed by the server 108 for monitoring disinfection of the device 104, according to one or more embodiments described herein. At step 1102, the server 108 includes means such as, the processor 1002 and/or the like, for receiving sensor data from the device 104 comprising a plurality of sensors 312, 314, 316, and 318, via the network 106. As discussed, the plurality of sensors 312, 314, 316, and 318 may correspond to touch sensors, light sensors, and/or the like. The sensors 312, 314, 316, and 318 can be positioned at a respective plurality of surfaces 212, 214, 216, 218, and 220 of the device 104. The sensor data indicates that a disinfecting agent is applied on one or more surfaces 212, 214, 216, 218, and 220 of the plurality of surfaces 212, 214, 216, 218, and 220 of the device 104.

In an embodiment, prior to receiving the sensor data, the server 108 includes means such as, the processor 1002 and/or the like, for receiving data associated with one or more touch inputs on the one or more surfaces 212, 214, 216, 218, and 220 of the plurality of surfaces 212, 214, 216, 218, and 220 of the device 104, from the device 104 via the network 106. In an embodiment, the device 104 is configured to detect the touch inputs as described in conjunction with FIG. 5. In an embodiment, the server 108 includes means such as, the processor 1002 and/or the like, for identifying the one or more surfaces 212, 214, 216, 218, and 220 for the disinfection by the disinfecting agent, based on the received data associated with the one or more touch inputs. In an embodiment, the processor 1002 is configured to identify the one or more surfaces 212, 214, 216, 218, and 220 as described in conjunction with FIG. 6. In an embodiment, the server 108 includes means such as, the processor 1002 and/or the like, for generating the second notification to indicate the one or more surfaces 212, 214, 216, 218, and 220 for the disinfection by the disinfecting agent. In an embodiment, the server 108 includes means such as, the processor 1002 and/or the like, for transmitting the second notification to the device 104 via the network 106.

At step 1104, the server 108 includes means such as, the processor 1002 and/or the like, for determining at least one exposure characteristic based on the sensor data. The at least one exposure characteristic is associated with disinfection of the one or more surfaces 212, 214, 216, 218, and 220 of the device 104 by the disinfecting agent. In an embodiment, the at least one exposure characteristic comprises at least one of a measure of moisture content on the one or more surfaces 212, 214, 216, 218, and 220 of the device 104, a first time duration associated with application of the disinfecting agent on the one or more surfaces 212, 214, 216, 218, and 220 of the device 104, a second time duration between subsequent instances of application of the disinfecting agent on the one or more surfaces 212, 214, 216, 218, and 220 of the device 104, a chemical property of the disinfecting agent, etc. The determination of the measure of the moisture content and the first time duration associated with the application of the disinfecting agent is further described in conjunction with FIG. 12. The determination of the second time duration between subsequent instances of application of the disinfecting agent is further described in conjunction with FIG. 8. The determination of the chemical property of the disinfecting agent is further described in conjunction with FIG. 9.

At step 1106, the server 108 includes means such as, the processor 1002 and/or the like, for comparing the at least one exposure characteristic to a threshold parameter associated with the at least one exposure characteristic. At step 1108, the server 108 includes means such as, the processor 1002 and/or the like, for determining whether the at least one exposure characteristic exceeds the threshold parameter. The comparison of the measure of the moisture content and the first time duration with respective threshold parameters is further described in conjunction with FIG. 12. The comparison of the second time duration with a threshold parameter is further described in conjunction with FIG. 8. The comparison of the chemical property of the disinfecting agent with a threshold parameter is further described in conjunction with FIG. 9.

At step 1110, the server 108 includes means such as, the processor 1002 and/or the like, for determining that the one or more surfaces 212, 214, 216, 218, and 220 are disinfected when the at least one exposure characteristic exceeds the threshold parameter. At step 1112, the server 108 includes means such as, the processor 1002 and/or the like, for generating a first notification indicating that the one or more surfaces 212, 214, 216, 218, and 220 of the device 104 are disinfected, in response to the comparison. In an embodiment, the first notification comprises, for example, a text message, an audio message, a vibration, a color-coded LED indicator, etc. The generation of the first notification based on the comparison of the measure of the moisture content and the first time duration with a moisture threshold parameter and a time threshold parameter, respectively, is further described in conjunction with FIG. 11. The generation of the first notification based on the comparison of the second time duration with a time interval threshold parameter is further described in conjunction with FIG. 8. The generation of the first notification based on the comparison of the chemical property of the disinfecting agent with a reference chemical property is further described in conjunction with FIG. 9. At step 1114, the server 108 includes means such as, the processor 1002 and/or the like, for transmitting the first notification to the device 104 via the network 106.

At step 1116, the server 108 includes means such as, the processor 1002 and/or the like, for determining at least one contaminated surface 212, 214, 216, 218, and 220 of the one or more surfaces 212, 214, 216, 218, and 220 when the at least one exposure characteristic does not exceed the threshold parameter. At step 1118, the server 108 includes means such as, the processor 1002 and/or the like, for generating a second notification to indicate the at least one contaminated surface 212, 214, 216, 218, and 220 for disinfection by the disinfecting agent. In an embodiment, the second notification comprises, for example, a text message, an audio message, a vibration, a color-coded LED indicator, etc. The generation of the second notification based on the comparison of the measure of the moisture content and the first time duration with a moisture threshold parameter and a time threshold parameter, respectively, is further described in conjunction with FIG. 12. The generation of the second notification based on the comparison of the second time duration with a time interval threshold parameter is further described in conjunction with FIG. 8. The generation of the second notification based on the comparison of the chemical property of the disinfecting agent with a reference chemical property is described later in conjunction with FIG. 9. At step 1120, the server 108 includes means such as, the processor 1002 and/or the like, for transmitting the second notification to the device 104 via the network 106.

FIG. 12 illustrates a flowchart 1200 of a method performed by the server 108 for monitoring the disinfection of the device 104 based on moisture content on the device 104, according to one or more embodiments described herein. At step 1202, the server 108 includes means such as, the processor 1002 and/or the like, for receiving the sensor data from the device 104 comprising the plurality of sensors 312, 314, 316, and 318. As discussed, in conjunction with FIG. 4, the plurality of sensors 312, 314, 316, and 318 may correspond to for example, touch sensors, light sensors, and/or the like.

At step 1204, the server 108 includes means such as, the processor 1002 and/or the like, for determining the measure of moisture content on the one or more surfaces 212, 214, 216, 218, and 220 based on the sensor data. As discussed above in conjunction with FIG. 3, changes in capacitance values of one or more surfaces 212, 214, 216, 218, and 220 may indicate moisture accumulation in the one or more surfaces 212, 214, 216, 218, and 220. Because the capacitance values of the one or more surfaces 212, 214, 216, 218, and 220 varies upon moisture accumulation, therefore, by monitoring the changes in the capacitance values, the measure of moisture content on the display screen 110 of the device 104 may be detected, as described in conjunction with FIG. 3.

At step 1206, the server 108 includes means such as, the processor 1002 and/or the like, for determining whether the measure of moisture content exceeds a moisture threshold parameter. At step 1208, the server 108 includes means such as, the processor 1002 and/or the like, for determining that the disinfecting agent is applied on the one or more surfaces 212, 214, 216, 218, and 220 when the measure of moisture content exceeds the moisture threshold parameter. In response to determining that the disinfecting agent is applied on the one or more surfaces 212, 214, 216, 218, and 220, the server 108 includes means such as, the processor 1002 and/or the like, for determining a time duration associated with application of the disinfecting agent on the one or more surfaces 212, 214, 216, 218, and 220 of the device 104. At step 1210, the server 108 includes means such as, the processor 1002 and/or the like, for determining whether the time duration associated with application of the disinfecting agent on the one or more surfaces 212, 214, 216, 218, and 220 exceeds a time threshold parameter. By performing the step 1210, the processor 1002 checks whether the measure of moisture content is greater than the moisture threshold parameter for a predetermined time duration. Accordingly, by performing the step 1210, the processor 1002 avoids false determination of the measure of moisture content being greater than the moisture threshold parameter.

At step 1212, in response to the determining that the time duration associated with application of the disinfecting agent exceeds the time threshold parameter, the server 108 includes means such as, the processor 1002 and/or the like, for generating the first notification to indicate that the one or more surfaces 212, 214, 216, 218, and 220 are disinfected. The first notification comprises, for example, a text message, an audio message, a vibration, a color-coded LED indicator, etc. At step 1214, the server 108 includes means such as, the processor 1002 and/or the like, for transmitting the first notification to the device 104 via the network 106.

At step 1216, the server 108 includes means such as, the processor 1002 and/or the like, for determining at least one contaminated surface 212, 214, 216, 218, and 220 of the one or more surfaces 212, 214, 216, 218, and 220 when the time duration associated with application of the disinfecting agent does not exceed the time threshold parameter. At step 1218, in response to the determining that at least one contaminated surface 212, 214, 216, 218, and 220, the server 108 includes means such as, the processor 1002 and/or the like, for generating the second notification to indicate the at least one contaminated surface 212, 214, 216, 218, and 220 of the one or more surfaces 212, 214, 216, 218, and 220 for disinfection by the disinfecting agent. The second notification comprises, for example, a text message, an audio message, a vibration, a color-coded LED indicator, etc. Further, at step 1210, in response to the determining that the time duration associated with application of the disinfecting agent does not exceed the time threshold parameter, the server 108 includes means such as, the processor 1002 and/or the like, for generating the second notification to indicate the at least one contaminated surface 212, 214, 216, 218, and 220 of the one or more surfaces 212, 214, 216, 218, and 220 for disinfection by the disinfecting agent. At step 1220, the server 108 includes means such as, the processor 1002 and/or the like, for transmitting the second notification to the device 104 via the network 106.

FIG. 13 illustrates a flowchart 1300 of a method performed by the server 108 for generating a plurality of disinfection models for monitoring the disinfection of a plurality of devices 104 and predicting disinfection trends associated with the plurality of devices 104, according to one or more embodiments described herein.

At step 1302, the server 108 includes means such as, the processor 1002, and/or the like, for receiving sensor data from a plurality of devices 104 communicatively coupled to the server 108 via the network 106. Each of the devices 104 comprises a plurality of sensors 312, 314, 316, and 318 configured to generate sensor data that indicates that a disinfecting agent is applied on one or more surfaces 212, 214, 216, 218, and 220 of the plurality of surfaces 212, 214, 216, 218, and 220 of the device 104. In an example embodiment, the sensor data may be collected from one or more users 102 each using their respective plurality of devices 104 of a same design model to avoid any deviations in the received sensor data that may be caused by variations in a design model or components of the plurality of devices 104. For example, the sensor data may be received from 100 smartphones of a same design model with same dimensions (such as length, width, height, weight, etc.) and same electronic components (such as sensors, processor, memory, etc.). In another embodiment, the collection of the sensor data is not limited to the plurality of devices 104 of a same design model but may also correspond to the plurality of devices 104 of different design models. In an embodiment, the sensor data received from each device 104 of the plurality of devices 104 may correspond to data associated with a change in capacitance value of each surface 212, 214, 216, 218, and 220 of a device 104 of the respective plurality of devices 104 that indicates moisture accumulation on each surface 212, 214, 216, 218, and 220 or that indicates evaporation rates of a respective disinfecting agent, a time duration associated with the changes in the capacitance values, etc.

At step 1304, the server 108 includes means such as, the processor 1002, and/or the like, for generating a disinfection monitoring dataset comprising a plurality of exposure characteristics associated with the plurality of devices 104 based on the sensor data. In an embodiment, the processor 1002 is configured to determine exposure characteristics associated with each device 104 of the plurality of devices 104, based on the received sensor data. In an embodiment, the exposure characteristics comprise a measure of moisture content on the one or more surfaces 212, 214, 216, 218, and 220 of the respective plurality of devices 104, a first time duration associated with application of the disinfecting agent on the one or more surfaces 212, 214, 216, 218, and 220 of the respective plurality of devices 104, a second time duration between subsequent instances of application of the disinfecting agent on the one or more surfaces 212, 214, 216, 218, and 220 of the respective plurality of devices 104, and/or chemical properties of different disinfecting agents, etc.

In an embodiment, the processor 1002 is configured to extract a plurality of features from the sensor data to generate the disinfection monitoring dataset. The plurality of features correspond to the plurality of exposure characteristics associated with the respective plurality of devices 104. For example, if the exposure characteristic corresponds to a measure of moisture content on the one or more surfaces 212, 214, 216, 218, and 220 of the device 104, the processor 1002 extracts features corresponding to changes in capacitance values of the one or more surfaces 212, 214, 216, 218, and 220 that indicates moisture accumulation on the one or more surfaces 212, 214, 216, 218, and 220. If the exposure characteristic corresponds to a first time duration associated with the application of the disinfecting agent on the one or more surfaces 212, 214, 216, 218, and 220 of the respective plurality of devices 104, the processor 1002 extracts features corresponding to a time duration at which a change in capacitance values is detected. If the exposure characteristic corresponds to a second time duration between subsequent instances of application of the disinfecting agent on the one or more surfaces 212, 214, 216, 218, and 220 of the respective plurality of devices 104, the processor 1002 extracts features corresponding to a first time duration and subsequent time durations that indicate time gaps between subsequent instances of application of the disinfecting agent on the one or more surfaces 212, 214, 216, 218, and 220. If the exposure characteristic corresponds to a chemical property of the disinfecting agent, the processor 1002 extracts features corresponding to evaporation rates of different disinfecting agents applied on the one or more surfaces 212, 214, 216, 218, and 220 of the respective plurality of devices 104.

At step 1306, the server 108 includes means such as, the processor 1002, and/or the like, for training a plurality of disinfection models associated with the plurality of exposure characteristics based on the disinfection monitoring dataset. In an embodiment, the processor 1002 employs conventional machine-learning algorithms such as, decision trees, k-nearest neighbors (KNN) algorithm, random forest, boosting, support vector machines (SVM), Apriori algorithm, K-means clustering, neural networks, Markov decision process, regression, logistic regression, etc., for training the plurality of disinfection models.

At step 1308, the server 108 includes means such as, the processor 1002, and/or the like, for determining a plurality of disinfection trends, based on the plurality of disinfection models. In an embodiment, each of the exposure characteristics forming the feature matrices are evaluated based on the generated disinfection model. Each exposure characteristic is fed as an input to a disinfection model of the plurality of disinfection models, and the processor uses the plurality of disinfection models to generate the plurality of disinfection trends. In an embodiment, the plurality of disinfection trends may be used to predict a type of a disinfecting agent to be applied to one or more surfaces 212, 214, 216, 218, and 220 of the device 104, to predict a duration for application of the disinfecting agent on the one or more surfaces 212, 214, 216, 218, and 220 of the device 104 to achieve complete disinfection of the device 104, to predict a time interval for periodic disinfection of the device 104 by the disinfecting agent, to identify users 102 who invest more amounts of disinfecting agents than users 102 who invest less amounts of disinfecting agent for disinfection of the plurality of devices 104, to predict damages and/or a lifecycle of the plurality of devices 104 based on the types of disinfecting agents used and/or duration of application of different disinfecting agents, to determine exposure of the plurality of devices 104 to water such as, to rain, full submersion in water, few drops of any liquid, etc.

In an example embodiment, the processor 1002 stores data associated with the disinfection monitoring dataset, the plurality of exposure characteristics, the sensor data, the plurality of disinfection models, the plurality of disinfection trends, etc., in a database implemented on a cloud computing environment. In another example embodiment, the processor 1002 stores data associated with the disinfection monitoring dataset, the plurality of exposure characteristics, the sensor data, the plurality of disinfection models, the plurality of disinfection trends, etc., in a database implemented on the server 108.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. A method for monitoring disinfection of a device, the method comprising:
    training a plurality of disinfection models associated with a plurality of exposure characteristics based on a disinfection monitoring dataset, wherein the disinfection monitoring dataset is based on disinfection monitoring data received from a plurality of external devices:
    determining, based on the plurality of disinfection models, a type of disinfecting agent and a duration for disinfecting agent application for disinfection of one or more surfaces of the device;
    activating, by a processor of the device, one or more sensors positioned at the one or more surfaces of the device in response to an interaction with one or more touch inputs on the one or more surfaces of the device;
    detecting, by the processor, sensor data at the one or more sensors, wherein the sensor data indicates that a disinfecting agent is applied on at least one of the one or more surfaces of the device based on a detected moisture and an evaporation rate calculated based on a signal from the one or more sensors;
    comparing, by the processor, the sensor data to the determined type of disinfecting agent and the determined duration for disinfecting agent application; and
    in response to the comparison, generating, by the processor, a first notification indicating that the one or more surfaces of the device are disinfected.

2. The method of claim 1, further comprising, prior to receiving the sensor data:
    in response to the detection, identifying, by the processor, the one or more surfaces for the disinfection by the disinfecting agent; and
    generating, by the processor, a second notification to indicate the one or more surfaces for the disinfection by the disinfecting agent.

3. The method of claim 1, further comprising:
    in response to the comparison, determining, by the processor, at least one contaminated surface of the one or more surfaces; and
    generating, by the processor, a third notification to indicate the at least one contaminated surface for the disinfection by the disinfecting agent.

4. The method of claim 1, further comprising determining a type of the disinfecting agent based on the comparison.

5. The method of claim 1, further comprising:
    transmitting, by the processor, the sensor data to a server via a network; and
    receiving, by the processor, the first notification from the server, wherein the server is configured to generate the first notification based on the comparison.

6. The method of claim 1, wherein the one or more sensors are one or more light sensors.

7. The method of claim 1, further comprising, prior to receiving the sensor data:
    in response to the detection of the one or more touch inputs, identifying, by the processor, the one or more surfaces for the disinfection by the disinfecting agent; and
    generating, by the processor, a second notification to indicate the one or more surfaces for the disinfection by the disinfecting agent.

8. A device comprising:
    one or more touch inputs;
    a plurality of sensors positioned at a respective plurality of surfaces of the device, wherein one or more sensors of the plurality of sensors are configured to detect sensor data indicating that a disinfecting agent is applied on one or more surfaces of the device based on a detected moisture and an evaporation rate calculated based on a signal from the one or more sensors; and
    a processor communicatively coupled to the plurality of sensors, wherein the processor is configured to:
        train a plurality of disinfection models associated with a plurality of exposure characteristics based on a disinfection monitoring dataset, wherein the disinfection monitoring dataset is based on disinfection monitoring data received from a plurality of external devices;
        determine, based on the plurality of disinfection models, a type of disinfecting agent and a duration for disinfecting agent application for disinfection of one or more surfaces of the device;
        activate the one or more sensors in response to an interaction with the one or more touch inputs on the one or more surfaces of the device from one or more touch sensors positioned at the respective surfaces;
        compare the sensor data to the determined type of disinfecting agent and the determined duration for disinfecting agent application; and
        in response to the comparison, generate a first notification indicating that the one or more surfaces of the device are disinfected.

9. The device of claim 8, prior to receiving the sensor data, wherein the processor is further configured to:
    in response to the detection, identify the one or more surfaces for the disinfection by the disinfecting agent; and
    generate a second notification to indicate the one or more surfaces for the disinfection by the disinfecting agent.

10. The device of claim 8, wherein the processor is further configured to:
    in response to the comparison, determine at least one contaminated surface of the one or more surfaces; and
    generate a third notification to indicate the at least one contaminated surface for the disinfection by the disinfecting agent.

11. The device of claim 8, wherein the processor is further configured to determine a type of the disinfecting agent based on the comparison.

12. The device of claim 8, wherein the processor is further configured to:
- transmit the sensor data to a server, via a network; and
- receive the first notification from the server, wherein the server is configured to generate the first notification based on the comparison.

13. A server comprising:
a processor configured to:
- train a plurality of disinfection models associated with a plurality of exposure characteristics based on a disinfection monitoring dataset, wherein the disinfection monitoring dataset is based on disinfection monitoring data received from a plurality of external devices;
- determine, based on the plurality of disinfection model, a type of disinfecting agent and a duration for disinfecting agent application for disinfection of one or more surfaces of the device;
- activate one or more sensors positioned at the one or more surfaces of the device in response to an interaction with one or more touch inputs on the one or more surfaces of the device;
- detect, sensor data at the one or more sensors, wherein the sensor data indicates that a disinfecting agent is applied on at least one of the one or more surfaces of the device based on a detected moisture and an evaporation rate calculated based on a signal from the one or more sensors;
- compare the sensor data to the determined type of disinfecting agent and the determined duration for disinfecting agent application; and
- in response to the comparison, generate a first notification indicating that the one or more surfaces of the device are disinfected wherein the processor is further configured to transmit the first notification to the device via the network.

14. The server of claim 13, prior to receiving the sensor data, wherein the processor is further configured to:
- receive, from the device via the network, data associated with the one or more touch inputs on the one or more surfaces of the plurality of surfaces of the device;
- identify the one or more surfaces for the disinfection by the disinfecting agent, based on the one or more touch inputs;
- generate a second notification to indicate the one or more surfaces for the disinfection by the disinfecting agent; and
- transmit the second notification to the device via the network.

15. The server of claim 13, wherein the processor is further configured to:
- in response to the comparison, determine at least one contaminated surface of the one or more surfaces;
- generate a third notification to indicate the at least one contaminated surface for the disinfection by the disinfecting agent; and
- transmit the third notification to the device via the network.

* * * * *